United States Patent
Hanson et al.

(10) Patent No.: US 10,575,855 B2
(45) Date of Patent: Mar. 3, 2020

(54) OCCLUSION DEVICE

(71) Applicant: Boston Scientific Scimed, Inc., Maple Grove, MN (US)

(72) Inventors: Cass A. Hanson, St. Paul, MN (US); Joseph M. Connolly, Minneapolis, MN (US); Katherine Routh, Coon Rapids, MN (US); Jaydeep Y. Kokate, Plymouth, MN (US); Gary J. Pederson, Albertville, MN (US); Derek C. Sutermeister, Ham Lake, MN (US); Michele C. Tessmer, Plymouth, MN (US); Jeffrey S. Lindquist, Maple Grove, MN (US); Robert N. Squire, Maple Grove, MN (US); Steven L. Kangas, Woodbury, MN (US); David Raab, Minneapolis, MN (US); Joel Munsinger, Blaine, MN (US); Derek K. Larson, Golden Valley, MN (US); Martin R. Willard, Burnsville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 726 days.

(21) Appl. No.: 15/085,999

(22) Filed: Mar. 30, 2016

(65) Prior Publication Data
US 2016/0287259 A1    Oct. 6, 2016

Related U.S. Application Data

(60) Provisional application No. 62/140,218, filed on Mar. 30, 2015.

(51) Int. Cl.
| | | |
|---|---|---|
| *A61B 17/12* | (2006.01) | |
| *A61M 25/10* | (2013.01) | |
| *A61B 17/00* | (2006.01) | |

(52) U.S. Cl.
CPC .. *A61B 17/12136* (2013.01); *A61B 17/12022* (2013.01); *A61B 17/12031* (2013.01);
(Continued)

(58) Field of Classification Search
CPC ........ A61B 17/12136; A61B 17/12022; A61B 17/12031; A61B 17/12109;
(Continued)

(56) References Cited

U.S. PATENT DOCUMENTS

| | | | | |
|---|---|---|---|---|
| 3,173,418 A | * | 3/1965 | Baran | .................. A61M 16/04 128/207.15 |
| 4,517,979 A | | 5/1985 | Pecenka | |

(Continued)

FOREIGN PATENT DOCUMENTS

| | | | | |
|---|---|---|---|---|
| DE | 2901701 | | 7/1980 | |
| EP | 0458649 A1 | * | 11/1991 | ....... A61B 17/12109 |

(Continued)

*Primary Examiner* — Ashley L Fishback

(57) ABSTRACT

Medical devices and methods for forming the medical devices are disclosed in the present application. In one illustrative example an occlusion balloon comprises an outer balloon member, and an inner balloon member having an inner wall and an outer wall and extending through at least a portion of the outer balloon member. In at least some examples, when forces acting on the inner wall of the inner balloon member equal forces acting on the outer wall of the inner balloon member, the inner balloon member defines a lumen.

17 Claims, 21 Drawing Sheets

(52) U.S. Cl.
CPC .. *A61B 17/12109* (2013.01); *A61B 17/12113* (2013.01); *A61B 2017/00526* (2013.01); *A61M 2025/1015* (2013.01)

(58) Field of Classification Search
CPC ... A61B 17/12113; A61B 2017/00526; A61M 25/1011; A61M 2025/1013; A61M 2025/1015
See application file for complete search history.

(56) References Cited

U.S. PATENT DOCUMENTS

| | | | |
|---|---|---|---|
| 5,181,921 A | | 1/1993 | Makita et al. |
| 5,222,970 A | * | 6/1993 | Reeves ............ A61B 17/12109 604/164.05 |
| 5,447,497 A | * | 9/1995 | Sogard ............... A61M 25/1011 604/101.02 |
| 6,293,960 B1 | | 9/2001 | Ken |
| 6,379,329 B1 | | 4/2002 | Naglreiter et al. |
| 9,313,826 B2 | * | 4/2016 | Akizuki ............ H04M 1/72502 |
| 2002/0049465 A1 | | 4/2002 | Meyer et al. |
| 2003/0220666 A1 | | 11/2003 | Mirigian et al. |
| 2004/0254625 A1 | | 12/2004 | Stephens et al. |
| 2007/0083158 A1 | * | 4/2007 | Hirszowicz ........ A61M 25/0119 604/96.01 |
| 2007/0244502 A1 | * | 10/2007 | Deutsch ........... A61B 17/00491 606/194 |
| 2008/0195137 A1 | | 8/2008 | Alleyne et al. |
| 2014/0207172 A1 | | 7/2014 | Bodewadt et al. |

FOREIGN PATENT DOCUMENTS

| | | | | |
|---|---|---|---|---|
| JP | 2007-533360 A | | 11/2007 | |
| WO | WO-9313826 A1 | * | 7/1993 | .......... A61M 25/104 |
| WO | 98/57586 | | 12/1998 | |

* cited by examiner

OCCLUSION DEVICE

CROSS-REFERENCE TO RELATED APPLICATION

This application claims the benefit of U.S. Provisional Application No. 62/140,218, entitled "Occlusion Device" and filed Mar. 30, 2015, which is hereby incorporated by reference in its entirety.

TECHNICAL FIELD

This disclosure relates to endovascular devices, and more particularly, to vaso-occlusive devices for the occlusion of body lumens and cavities.

BACKGROUND

In many clinical situations, blood vessels are occluded for a variety of purposes, such as to control bleeding, to prevent blood supply to tumors, to block blood flow within an aneurysm, or for prophylactic purposes, such as prophylactic gastroduodenal embolization or prophylactic hypogastric embolization. Vaso-occlusive devices are surgical implants placed within blood vessels or vascular cavities, typically by the use of a catheter, to form an occlusion at the site. Some vaso-occlusive devices may be inflated with materials that harden into solid masses, while other vaso-occlusive devices may have thrombogenic properties and cause a thrombus to form. The properties of the vaso-occlusive devices may cause a blockage of blood flow past the vaso-occlusive devices or into cavities where the vaso-occlusive devices were placed.

SUMMARY

This disclosure relates to endovascular devices, and more particularly, to vaso-occlusive devices for the occlusion of body lumens and cavities. In one embodiment, an occlusion balloon may comprise an outer balloon member, and an inner balloon member having an inner wall and an outer wall and extending through at least a portion of the outer balloon member, wherein when forces acting on the inner wall of the inner balloon member equal forces acting on the outer wall of the inner balloon member, the inner balloon member defines a lumen.

Alternatively, or additionally, in the above embodiment, the inner balloon member forms a seal when the occlusion balloon is inflated.

Alternatively, or additionally, in any of the above embodiments, when forces acting inward on the outer wall of the inner balloon member are greater than forces acting outward on the inner wall of the inner balloon member, the inner wall of the inner balloon member collapses radially inward.

Alternatively, or additionally, in any of the above embodiments, when the inner wall of the inner balloon member collapses radially inward, the inner balloon member forms a seal.

Alternatively, or additionally, in any of the above embodiments, when forces acting inward on the outer wall of the inner balloon member are greater than forces acting outward on the inner wall of the inner balloon member, the inner wall of the inner balloon member collapses against the outer balloon member.

Alternatively, or additionally, in any of the above embodiments, the inner balloon member is attached to the outer balloon member.

Alternatively, or additionally, in any of the above embodiments, the outer balloon member folds inward at one end to form the inner balloon member.

Alternatively, or additionally, in any of the above embodiments, the occlusion balloon has a proximal end and a distal end, and wherein the proximal end of the occlusion balloon comprises a funnel.

Alternatively, or additionally, in any of the above embodiments, the outer balloon member has a first compliance and the inner balloon member has a second compliance, wherein the first compliance is different than the second compliance.

Alternatively, or additionally, in any of the above embodiments, the first compliance is greater than the second compliance.

Alternatively, or additionally, in any of the above embodiments, the second compliance is greater than the first compliance.

Alternatively, or additionally, in any of the above embodiments, the occlusion balloon may further comprise a tubular member having a proximal end and a distal end, wherein the proximal end of the tubular member is connected to the outer balloon member and the distal end of the tubular member is connected to the inner balloon member.

Alternatively, or additionally, in any of the above embodiments, the outer balloon member has a first compliance, the inner balloon member has a second compliance, and the tubular member has a third compliance, wherein the third compliance less than the second compliance.

Alternatively, or additionally, in any of the above embodiments, the outer balloon member extends from a proximal end along a first central longitudinal axis to a distal end, and wherein the inner balloon member extends through at least a portion of the balloon member along a second central longitudinal axis that is parallel with the first central longitudinal axis.

Alternatively, or additionally, in any of the above embodiments, the second central longitudinal axis is coaxial with the first central longitudinal axis.

Alternatively, or additionally, in any of the above embodiments, the occlusion balloon may further comprise an adhesive disposed on the inner wall of the inner balloon member.

Alternatively, or additionally, in any of the above embodiments, the occlusion balloon may further comprise an adhesive disposed on the outer balloon member.

In another embodiment, an occlusion balloon may comprise a balloon member having a proximal end and a distal end, and a first solid self-sealing member disposed at the proximal end of the balloon member.

Alternatively, or additionally, in the above embodiment, the distal end of the balloon member is sealed.

Alternatively, or additionally, in any of the above embodiments, the occlusion balloon may further comprise a second solid self-sealing member disposed at the distal end of the balloon member.

Alternatively, or additionally, in any of the above embodiments, the first solid self-sealing member is configured to maintain a seal on the balloon member while allowing a shaft of up to 0.015 inches in diameter to pass through the first solid self-sealing member and into the balloon.

In yet another embodiment, an occlusion balloon may comprise an outer balloon member having a first compliance, and an inner balloon member extending through at least a portion of the outer balloon member and having a second compliance, the first compliance being different than the second compliance. In at least some further embodiments, the occlusion balloon is self-sealing.

Alternatively, or additionally, in the above embodiment, the first compliance is greater than the second compliance.

Alternatively, or additionally, in any of the above embodiments, the second compliance is greater than the first compliance.

Alternatively, or additionally, in any of the above embodiments, the inner balloon member is attached to the outer balloon member.

Alternatively, or additionally, in any of the above embodiments, wherein the occlusion balloon may further comprise a tubular member having a proximal end and a distal end, wherein the inner balloon member is attached to the distal end of the tubular member and the outer balloon member is attached to the proximal end of the tubular member.

Alternatively, or additionally, in any of the above embodiments, the tubular member has a third compliance, and wherein third compliance is less than the second compliance.

Alternatively, or additionally, in any of the above embodiments, the outer balloon member folds inward at one end to form the inner balloon member.

Alternatively, or additionally, in any of the above embodiments, a proximal end of the occlusion balloon comprises a funnel.

Alternatively, or additionally, in any of the above embodiments, the inner balloon member is configured to collapse to form a seal when the occlusion balloon is inflated.

Alternatively, or additionally, in any of the above embodiments, the inner balloon member is configured to collapse against itself to form the seal.

Alternatively, or additionally, in any of the above embodiments, the inner balloon member is configured to collapse against the outer balloon member to form the seal.

Alternatively, or additionally, in any of the above embodiments, the outer balloon member is non-compliant.

In still another embodiment, a method for forming a self-sealing occlusion balloon may comprise forming a balloon member having a tapered neck and having a first compliance, and attaching a hollow tube having a second compliance to the tapered neck, wherein the first compliance is different than the second compliance. In at least some embodiments, the method may further include inverting the hollow tube so that the hollow tube extends into the balloon member.

Alternatively, or additionally, in the above embodiment, the method may further comprise attaching a hollow tube having a third compliance to the tapered neck, and attaching the hollow tube having the second compliance to the hollow tube having the third compliance.

In another embodiment, an occlusion balloon may comprise a balloon member having a proximal end and a distal end, and a first solid self-sealing member disposed at the proximal end of the balloon member.

Alternatively, or additionally, in the above embodiment, the distal end of the balloon member is sealed.

Alternatively, or additionally, in any of the above embodiments, the occlusion balloon may further comprise a second solid self-sealing member disposed at the distal end of the balloon member.

Alternatively, or additionally, in any of the above embodiments, the first solid self-sealing member is configured to maintain a seal on the balloon member while allowing a shaft of up to 0.015 inches in diameter to pass through the first solid self-sealing member and into the balloon.

Alternatively, or additionally, in any of the above embodiments, the balloon member is porous to blood.

Alternatively, or additionally, in any of the above embodiments, the first solid self-sealing member is comprised of one or more of polyurethane, silicone, and styrene ethylene butylene styrene (SEBS).

Alternatively, or additionally, in any of the above embodiments, the occlusion balloon may further comprise an adhesive disposed on an outer surface of the balloon member.

Alternatively, or additionally, in any of the above embodiments, the occlusion balloon may further comprise a super absorbent hydrogel polymer disposed within a lumen of the balloon member.

Alternatively, or additionally, in any of the above embodiments, may further comprise a hollow tube defining a lumen extending through at least a portion of the balloon member, and wherein the hollow tube has one or more ports which open into a lumen of the balloon member.

Alternatively, or additionally, in any of the above embodiments, the hollow tube extends between the proximal end and the distal end of the balloon member.

In another embodiment, a method of forming an occlusion balloon may comprise forming a hollow tubular member, the hollow tubular member having a proximal end and a distal end, and forming a balloon member over at least a portion of the hollow tubular member. In at least some embodiments, the method may further comprise connecting a first solid self-sealing member to the proximal end of the hollow tubular member.

Alternatively, or additionally, in the above embodiment, the method may further comprise forming one or more inflation ports on the hollow tubular member.

Alternatively, or additionally, in any of the above embodiments, the method may further comprise sealing the distal end of the hollow tubular member.

Alternatively, or additionally, in any of the above embodiments, the method may further comprise connecting a second solid self-sealing member to the distal end of the hollow tubular member.

Alternatively, or additionally, in any of the above embodiments, the first solid self-sealing member is configured to maintain a seal on the balloon member while allowing a shaft of up to 0.015 inches in diameter to pass through the first solid self-sealing member and into the balloon.

Alternatively, or additionally, in any of the above embodiments, the first solid self-sealing member is comprised of a low-durometer material.

Alternatively, or additionally, in any of the above embodiments, the first solid self-sealing member is comprised of one or more of polyurethane, silicone, and styrene ethylene butylene styrene (SEBS).

Alternatively, or additionally, in any of the above embodiments, the method may further comprise disposing an adhesive on an outer surface of the balloon member.

Alternatively, or additionally, in any of the above embodiments, may further comprise disposing a super absorbent hydrogel polymer within a lumen of the balloon member.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF THE DRAWINGS

The disclosure may be more completely understood in consideration of the following detailed description of various embodiments in connection with the accompanying drawings, in which.

Figure 1A:
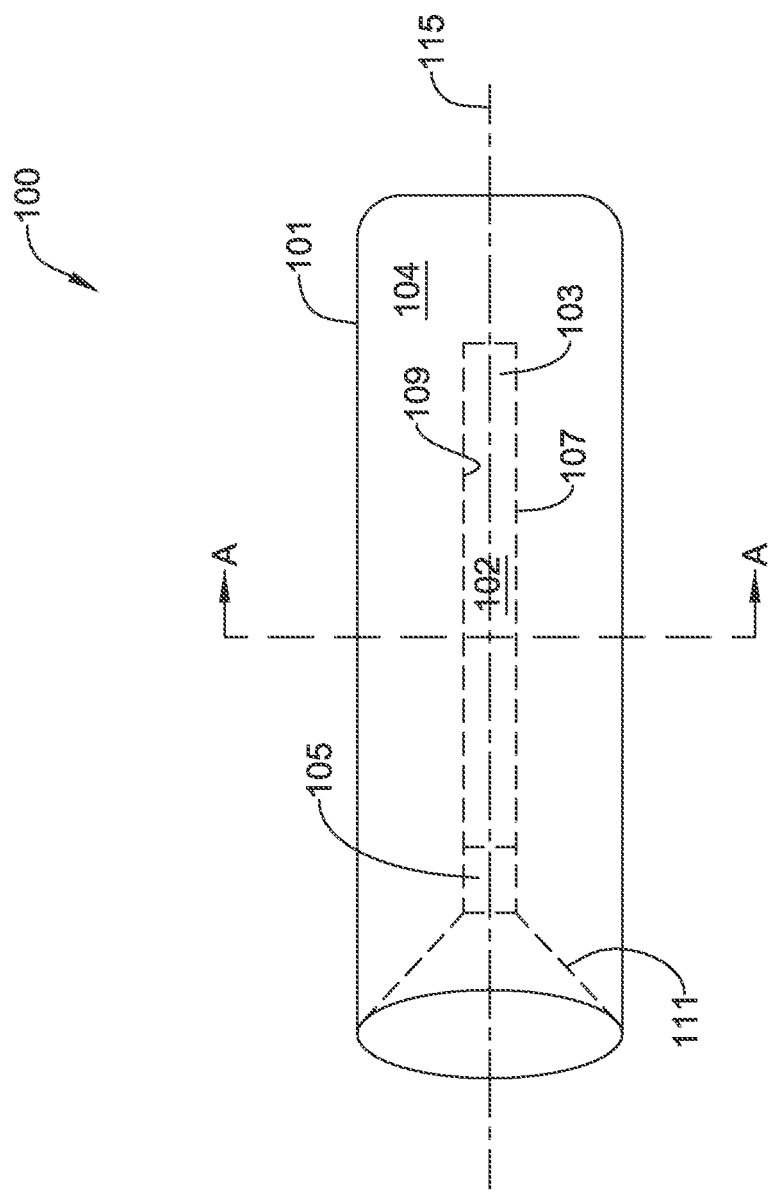
FIG. 1A is a side plan view of an exemplary occlusion balloon in accordance with various embodiments of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended to be only exemplary. Selected features of any illustrative embodiments may be incorporated into any other described embodiments unless clearly stated to the contrary.

FIG. 1A depicts an exemplary occlusion balloon 100. Occlusion balloon 100 may be used, for example, to occlude various vessels or arteries such as a right gastric artery, a gastroduodenal artery, right or left hepatic arteries, and gonadal veins. However, in other instances, occlusion device 100 may be used to occlude other body lumens, such as other arteries or vessels, or various vascular anomalies such as gastric varices. Occlusion balloon 100 may be comprised of outer balloon member 101 and inner balloon member 103, where inner balloon member 103 has an outer wall 107 (i.e., radially outward facing wall) and an inner wall 109 (i.e., radially inward facing wall). As seen in FIG. 1A, inner balloon member 103 may generally be disposed within outer balloon member 101. In some examples, inner balloon member 103 may extend through outer balloon member 101 in a concentric manner (i.e., with the central longitudinal axis of inner balloon member 103 coaxial with the central longitudinal axis of outer balloon member 101), although in other examples, inner balloon member 103 may extend through outer balloon member 101 in various off-center positions (e.g., with the central longitudinal axis of inner balloon member 103 parallel to, but offset to the central longitudinal axis of outer balloon member 101). For example, outer balloon member 101 may extend along a first central longitudinal axis 115, and inner balloon member 103 may extend along a second central longitudinal axis (not shown in FIG. 1A). In some instances, the first central longitudinal axis may be coaxial with the second central longitudinal axis, as in FIG. 1A. However, in other instances, the second central longitudinal axis may be offset from the first longitudinal central axis.

As shown in FIG. 1A, inner balloon member 103 may extend through outer balloon member 101 greater than half the length of outer balloon member 101. However, in other examples, inner balloon member 103 may extend through outer balloon member 101 varying distances. For example, inner balloon member 103 may extend through outer balloon member 101 anywhere between one-quarter of the length of outer balloon member 101 to almost the entire length of outer balloon member 101, in some instances. Generally, the greater the length that inner balloon member 103 extends through outer balloon member 101, the better the seal that may be formed.

In some embodiments, outer balloon member 101 may be generally non-compliant, while inner balloon member 103 is generally compliant. In other embodiments, however, both outer balloon member 101 and inner balloon member 103 may be compliant, with outer balloon member 101 having a first compliance and inner balloon member 103 having a second compliance. In these cases, the first compliance may generally be less than the second compliance. As will be described in more detail later, this difference in compliance between outer balloon member 101 and inner balloon member 103 may assist in the sealing of occlusion balloon 100.

Figure 1B:
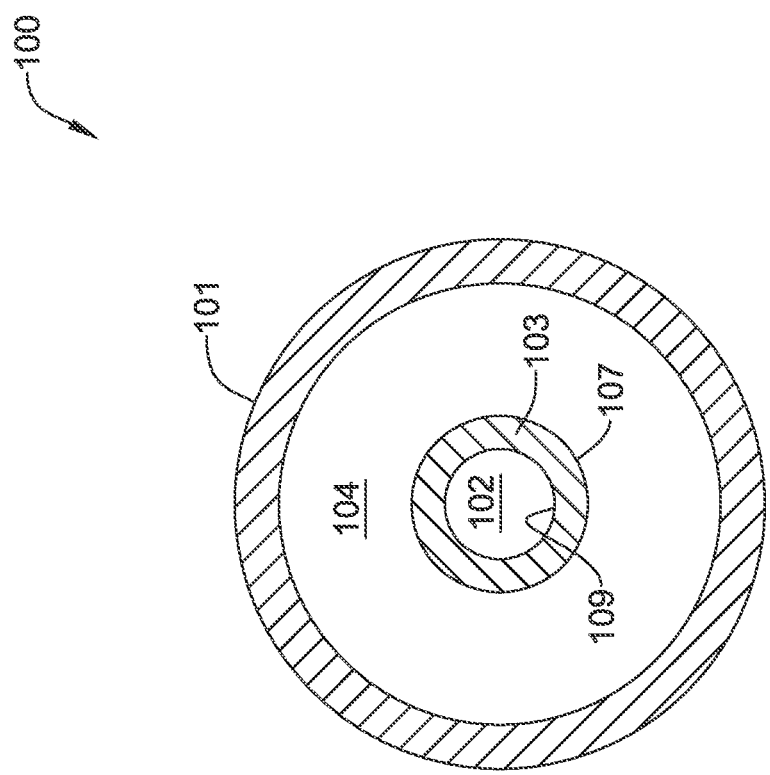
FIG. 1B depicts a cross-section of the occlusion balloon of FIG. 1A taken along line A-A in FIG. 1A.

In some examples, inner balloon member 103 may be attached to outer balloon member 101. For instance, outer balloon member 101 may fold inward to form inner balloon member 103 or be attached to inner balloon member 103. As seen in FIGS. 1A-1B, the diameter of outer balloon member 101 may be larger than the diameter of inner balloon member 103. Accordingly, as outer balloon member 101 folds inward to form inner balloon member 103 or be attached to inner balloon member 103, outer balloon member 101 may taper down to the diameter of inner balloon member 103, forming cone 111. In some instances, tubular member 105 may be disposed between outer balloon member 101 and inner balloon member 103. Where tubular member 105 is included, tubular member 105 may have a third compliance as compared to the first and second compliance of outer balloon member 101 and inner balloon member 103. In some instances, the third compliance may be less than both the first compliance and the second compliance. However, in other instances, the third compliance may be less than only the first compliance.

Where outer balloon member 101 is formed separate from inner balloon member 103 and later attached to inner balloon member 103, tubular member 105 may allow for easier attachment of outer balloon member 101 to inner balloon member 103. In examples where tubular member 105 has a compliance low enough, e.g. a high enough stiffness, to withstand internal pressures of occlusion balloon 100 when occlusion balloon 100 is inflated, tubular member 105 may act as a reservoir for retaining various particles or materials. For example, in some instances occlusion balloon 100 may be implanted prior to the delivery of various therapeutic particles or other small materials. Cone 111 may act to urge any such materials that get pushed against occlusion balloon 100 into tubular member 105, where the materials may be retained. This may act to keep such materials from getting stuck between occlusion balloon 100 and the wall of the artery or vessel where occlusion balloon 100 is implanted, as a means of mitigating potential harm to the artery or vessel or the patient. Cone 111 may further act as a centering member for inflation member 200 (shown in FIG. 2) or another retrieval member. For example, in some instances, occlusion balloon 100 may need to be deflated and removed from a patient. After positioning a retrieval member at the implant site, cone 111 may help to guide the retrieval member into lumen 102.

FIG. 1B depicts a cross-section of occlusion balloon 100 of FIG. 1A in an uninflated state as viewed along line A-A and may represent a steady-state configuration of occlusion balloon 100 whereby no net forces are acting on occlusion balloon 100. More specifically, FIG. 1A may depict a steady-state configuration whereby the forces acting on outer wall 107 of inner balloon member 103 are equal to the forces acting on inner wall 109 of inner balloon member 103. As can be seen in FIG. 1B, inner balloon member 103 may define lumen 102 and outer balloon member 101 may define lumen 104, where lumen 102 is generally smaller in diameter than lumen 104.

Figure 2:
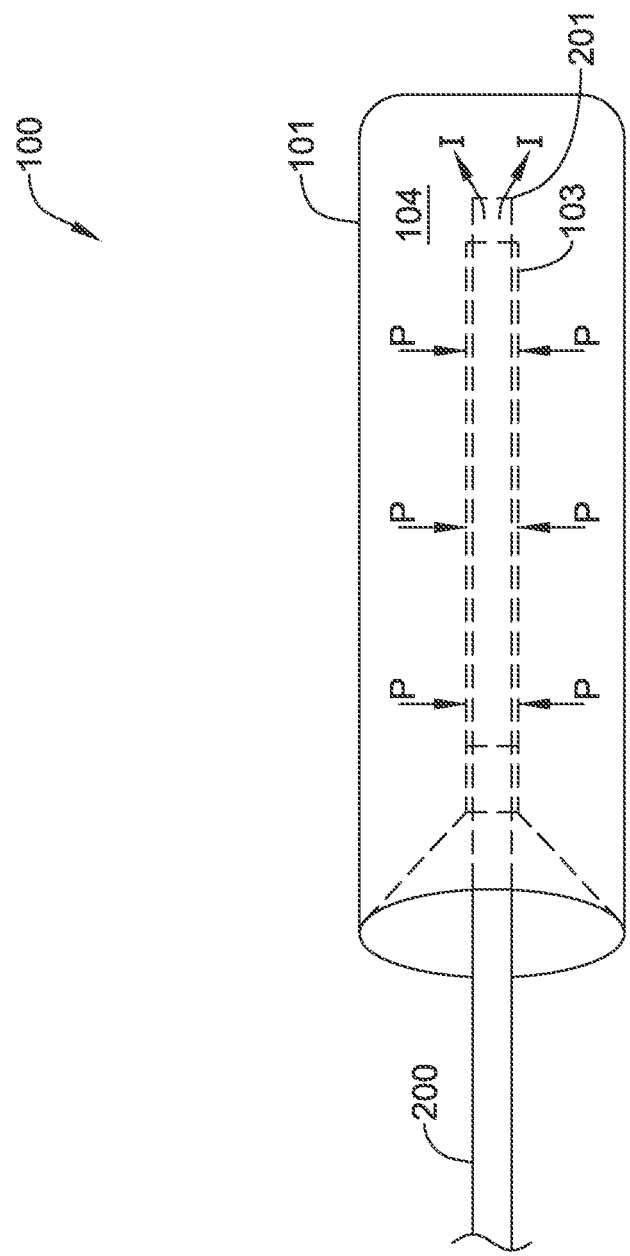
FIG. 2 is a side plan view of an exemplary occlusion balloon and inflation member in accordance with various embodiments of the present disclosure.

To implant and inflate occlusion balloon 100, occlusion balloon 100 may be disposed at a distal end of an inflation member 200, as shown in FIG. 2. Inflation member 200 may be a catheter or microcatheter, for example, and may include one or more inflation lumens extending through the length of inflation member 200. Different portions of inflation member 200 may have varying levels of rigidity. For instance, a proximal portion of inflation member 200 may have a relatively high rigidity, while the distal portion of inflation member 200 may have a relatively low level of rigidity. These differing levels of rigidity may allow for a user, such as a physician, to apply pushing forces to inflation member 200, yet allow at least the distal portion of inflation member 200 to bend through potentially tortuous paths to be positioned at a desired implant site.

In different embodiments, occlusion balloon 100 may have one or more different features to assist in retaining occlusion balloon 100 on inflation member 200. For instance, in some examples, inner balloon member 103 may generally define a wavy or tortuous path or lumen. Accordingly, when inflation member 200 is inserted into lumen 102 of inner balloon member 103, inner wall 109 of inner balloon member 103 may press against inflation member 200 at various locations on the distal portion of inflation member 200. The pressure between inner wall 109 and inflation member 200 may create sufficient friction between inner wall 109 and inflation member 200 to retain occlusion balloon 100 on inflation member 200 during implantation. In alternative embodiments, inflation member 200 may include an adhesive disposed on the outer surface of the distal portion of inflation member 200 that is inserted into lumen 102 of inner balloon member 103, and the adhesive may secure inflation member 200 to occlusion balloon 100. In these examples, the adhesive may be soluble to the inflation media. Accordingly, when the inflation media is delivered into outer balloon member 101, some of the inflation media will contact the adhesive and work to break the adhesive down, thereby releasing inflation member 200 from occlusion balloon 100. Of course, other embodiments may employ both of these retention techniques, if desired.

Once disposed at the desired implant site, the user may deliver inflation media through the one or more inflation lumens of inflation member 200. The inflation media may exit inflation member 200 near distal end 201 of inflation member 200, as represented by arrows I in FIG. 2, into lumen 104 of outer balloon member 101. As the inflation media is delivered into lumen 104 of outer balloon member 101, the internal pressure of occlusion balloon 100 rises, which places pressure onto inner balloon member 103, as shown by arrows P.

Figure 3A:
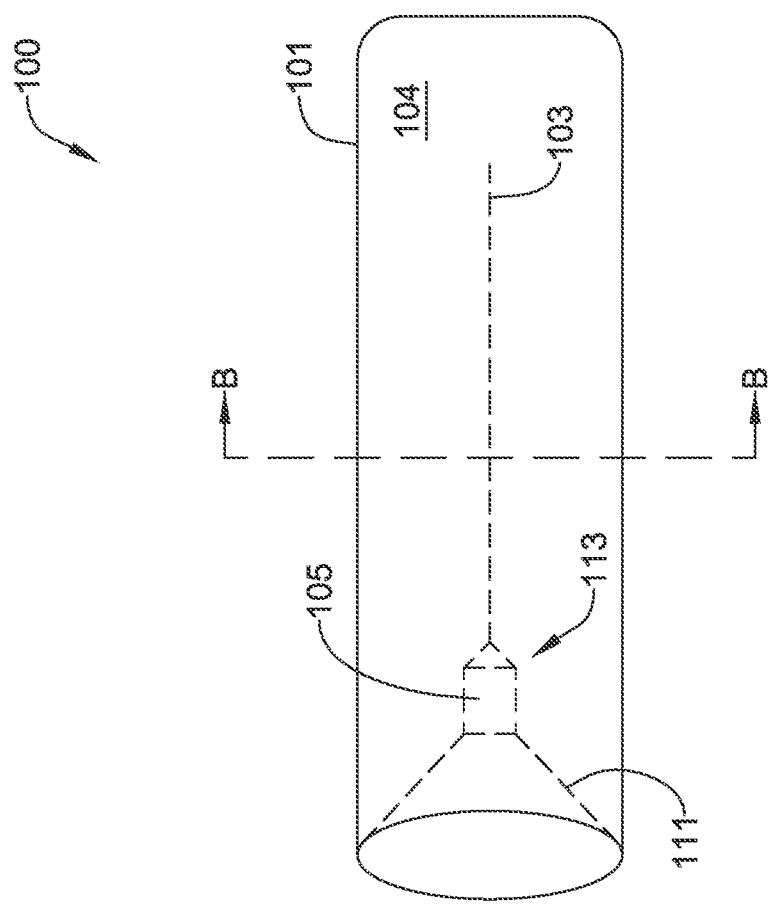
FIG. 3A is a side plan view of an exemplary occlusion balloon in an inflated state in accordance with various embodiments of the present disclosure.

FIG. 3A depicts occlusion balloon 100 in an inflated state after inflation member 200 has been removed. Where outer balloon member 101 is non-compliant, outer balloon member 101 may not expand appreciably or at all due to the pressure caused by the inflation media. In such instances, the resulting internal pressure from the inflation media may cause inner wall 109 of the generally more compliant inner balloon member 103 to collapse radially inward together to collapse the lumen 102 and form a seal. For instance, the internal pressure causes the forces inward on outer wall 107 of inner balloon member 103 to be greater than any forces acting outward on inner wall 109. In examples where tubular member 105 is included, and has a low-enough compliance to withstand the pressure from the inflation media, tubular member 105 may not collapse with inner balloon member 103, thus there may be a transition region 113 where the walls of inner balloon member 103 collapse down together to where they press together. Where outer balloon member 101 is compliant to some degree, the relative difference in the levels of compliance between outer balloon member 101 and inner balloon member 103 may still be sufficient for the internal pressure of occlusion balloon 100 after inflation to cause inner wall 109 of inner balloon member 103 to collapse radially inward together to collapse the lumen 102 and form a seal.

Figure 3B:
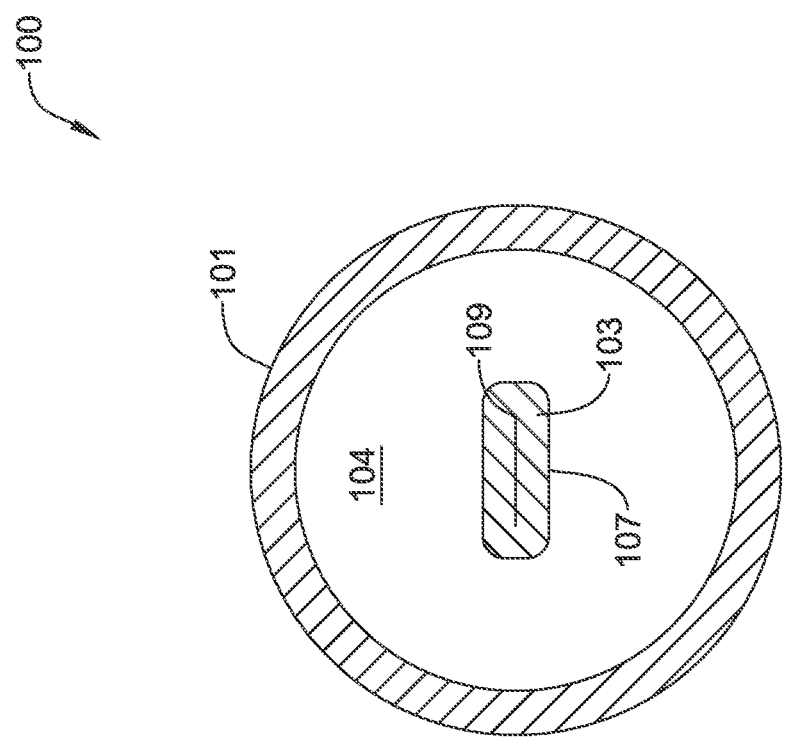
FIG. 3B depicts a cross-section of the inflated occlusion balloon of FIG. 3A taken along line B-B in FIG. 3A.

FIG. 3B depicts a cross-section of the inflated occlusion balloon 100 of FIG. 3A, as viewed along line B-B. As shown, the pressure from the inflation media has caused inner walls 109 to collapse together to form a seal. In this manner, occlusion balloon 100 may self-seal to prevent the inflation media disposed in lumen 104 of outer balloon member 101 from escaping lumen 104. In some instances, inner wall 109 of inner balloon member 103 may further include an adhesive. Accordingly, when inner wall 109 collapses together, the adhesive may work to further help seal outer balloon member 101 and maintain the seal of outer balloon member 101 even if the internal pressure within occlusion balloon 100 is later lost. In such examples, the adhesive may only have a high affinity for itself so that when inflation member 200 is inserted within lumen 102, the adhesive does not adhere inner wall 109 to inflation member 200. In other instances, inner wall 109 may include a water absorbable material, such as a water absorbable polymer. In such examples, the inflation media may at least include water. When the water contacts the water absorbable material, the material may swell to close up lumen 102. The swollen material may act in conjunction with the internal pressure of occlusion balloon 100 to form a seal.

In different embodiments than those described above, inner balloon member 103 may not have a relatively high compliance. Rather, inner balloon member 103 may have a low-enough compliance, e.g. high-enough stiffness, to not collapse under the internal pressure of occlusion balloon 100 when occlusion balloon 100 is inflated. Instead, inner balloon member 103 may further comprise a one-way valve disposed somewhere in lumen 102. In still some other alternative embodiments, inner wall 109 may include one or more thrombus forming compounds. In these embodiments, occlusion balloon 100 may be inflated with the patient's own blood, which after passing through lumen 102 and contacting the one or more thrombus forming compounds, may coagulate and form a thrombus in lumen 104 of outer balloon member 101.

Figure 4A:
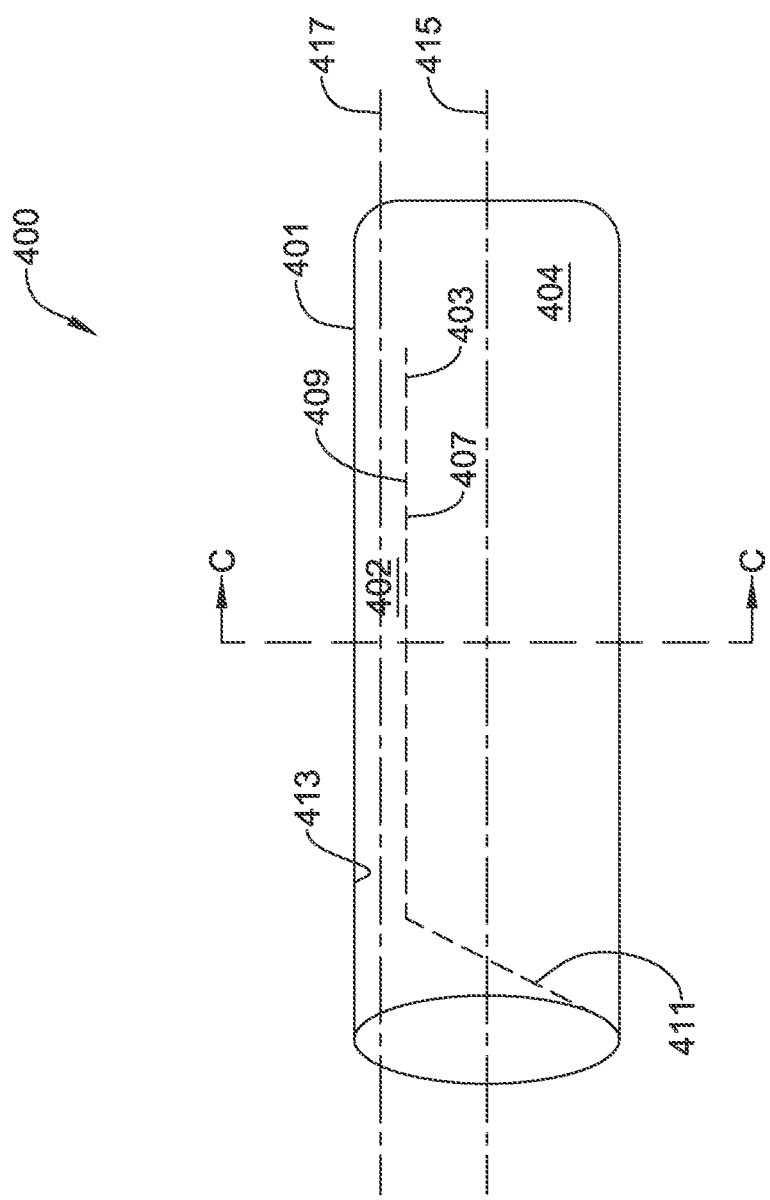
FIG. 4A is a side plan view of another exemplary occlusion balloon in accordance with various embodiments of the present disclosure.

FIG. 4A depicts another embodiment of an occlusion balloon, occlusion balloon 400. Like occlusion balloon 100, occlusion balloon 400 may be used to occlude various vessels or arteries such as a right gastric artery, a gastroduodenal artery, right or left hepatic arteries, or gonadal veins. However, in other instances, occlusion device 400 may be used to occlude other body lumens, such as other arteries or vessels, or various vascular anomalies such as gastric varices. Occlusion balloon 400 may have similar properties and a similar shape to occlusion balloon 100. For instance, occlusion balloon 400 may have outer balloon member 401 and inner balloon member 403. Additionally, outer balloon member 401 may fold inward to form inner balloon member 403 or attach to inner balloon member 403, thereby forming cone 411. However, unlike occlusion balloon 100, lumen 402 is defined partially by inner balloon member 403 and partially by outer balloon member 401. For instance, one wall of lumen 402 may be defined by an inner wall 409 of inner balloon member 402, while another wall of lumen 402 may be defined by an inner wall 413 of outer balloon member 401. In the example of FIG. 4A, outer balloon member 401 may extend along a first central longitudinal axis 415, and inner balloon member 403 may extend along a second central longitudinal axis, 417. As shown in the example of FIG. 4A, second central longitudinal axis 417 may be offset from first longitudinal central axis 415.

Figure 4B:
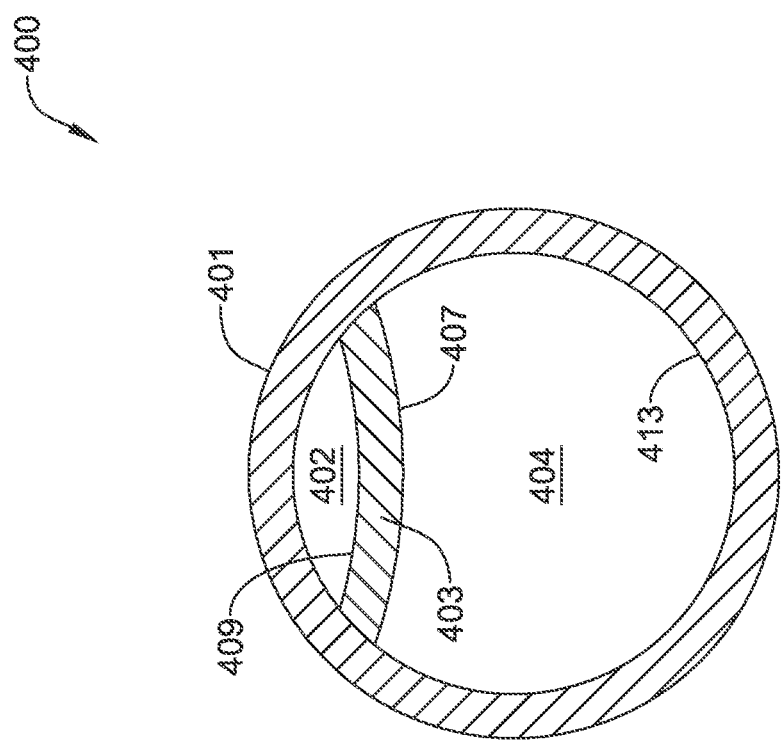
FIG. 4B depicts a cross-section of the occlusion balloon of FIG. 4A taken along line C-C in FIG. 4A in an un-inflated state.

FIG. 4B depicts a cross-section of occlusion balloon 400 in an uninflated state as viewed along line C-C. The configuration shown in 4B may represent occlusion balloon 400 in a steady state where no net forces are acting on occlusion balloon 400. More specifically, FIG. 4B may depict a steady-state configuration whereby the forces acting on outer wall 407 of inner balloon member 403 are equal to the forces acting on inner wall 409 of inner balloon member 403. In the steady state configuration, outer balloon member 401, in conjunction with outer wall 407 of inner balloon member 403, may define lumen 404. Additionally, outer balloon member 401, in conjunction with inner wall 409 of inner balloon member 403, may define lumen 402. Occlusion balloon 400 may be implanted and inflated in a similar manner to that described with respect to occlusion balloon 100. For example, occlusion balloon 400 may be disposed on a distal end of an inflation member, such as a catheter or microcatheter including one or more inflation lumens. Once positioned at a desired implant site, occlusion balloon 400 may be inflated by delivering inflation media through the inflation member and into lumen 404.

Figure 4C:
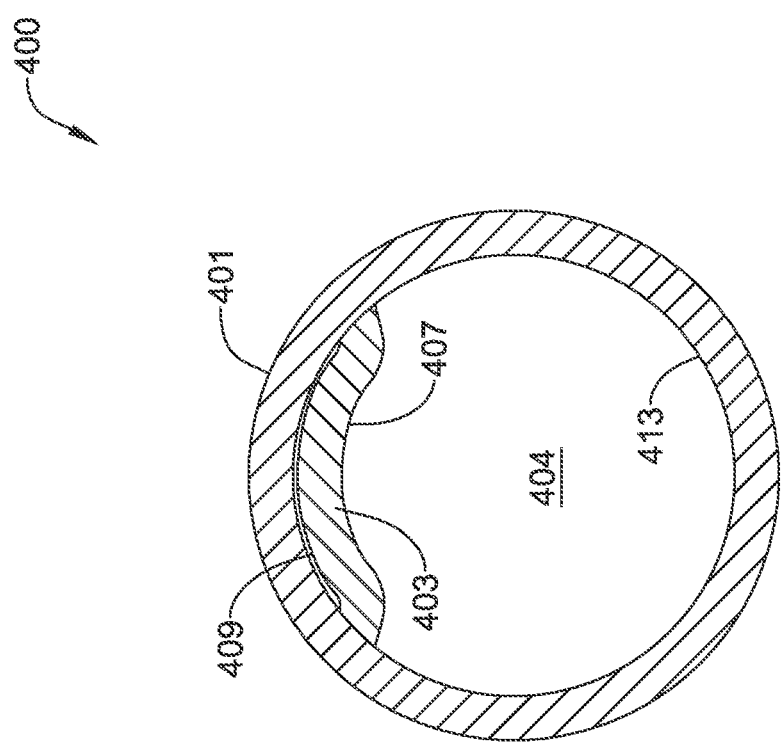
FIG. 4C depicts a cross-section of the occlusion balloon of FIG. 4A taken along line C-C in FIG. 4A in an inflated state.

FIG. 4C depicts a cross-section of occlusion balloon 400 in an inflated state, as viewed along line C-C. When occlusion balloon 400 is inflated, internal pressure may cause inner wall 409 of inner balloon member 403 to collapse against outer balloon member 401. For example, the internal pressure causes the forces inward on outer wall 407 of inner balloon member 403 to be greater than any forces acting outward on inner wall 409. As shown, the internal pressure may cause inner wall 409 of inner balloon member 403 to collapse against inner wall 413 of outer balloon member 401, and thus collapse lumen 402 and form a seal, thereby sealing the inflation media within occlusion balloon 400. In this manner, occlusion balloon 400 may self-seal to prevent the inflation media disposed within lumen 404 from escaping occlusion balloon 400. In some examples, the surface of inner wall 409 may contain an adhesive, similar to the adhesive described with respect to occlusion balloon 100.

In some embodiments of occlusion balloon 400, outer balloon member 401 may have a greater compliance than inner balloon member 403, as opposed to the other way around. In these embodiments, the internal pressure created by the inflation media may cause outer balloon member 401 to stretch to a greater extent than inner balloon member 403. The greater stretching by outer balloon member 401 than inner balloon member 403 may further facilitate the collapsing of inner wall 409 of inner balloon member 401 against outer balloon member 403. However, in other embodiments, outer balloon member 401 may have a lower compliance than inner balloon member 403, as is the case in some embodiments of occlusion balloon 100. Additionally, although not explicitly described with respect to occlusion balloon 400, in some examples occlusion balloon 400 may further include a tubular member, similar to tubular member 105 of occlusion balloon 100, disposed between outer balloon member 401 and inner balloon member 403.

Figure 5:
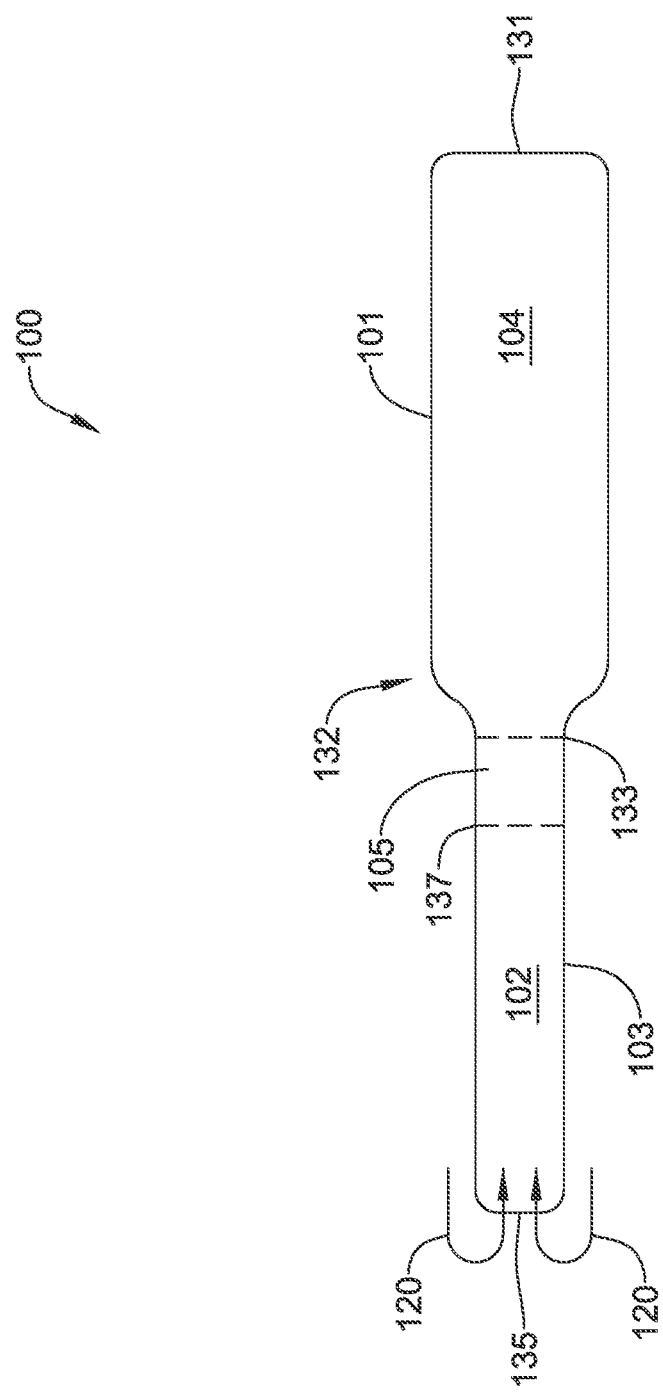
FIG. 5 is a side plan view of an exemplary occlusion balloon in accordance with various embodiments of the present disclosure.

FIG. 5 depicts occlusion balloon 100 in an unfolded state during a process of forming occlusion balloon 100. As shown, outer balloon member 101 may have a distal end 131 and a proximal end 133. Inner balloon member 103 may have distal end 137 and proximal end 135. Additionally, the outer diameter of outer balloon member 101 may taper down in region 132 so that the diameter of proximal end 133 is less than the diameter of distal end 131. In some cases, the diameter of proximal end 133 may be approximately the same as the diameter of distal end 137 of inner balloon member 103.

In some embodiments, outer balloon member 101 may be formed separately from inner balloon member 103. Where occlusion balloon 100 includes tubular member 105, proximal end 133 of outer balloon member 101 may be attached to a first end of tubular member 105. Inner balloon member 103 may be attached to a second end of tubular member 105. However, in examples where occlusion balloon 100 does not include tubular member 105, proximal end 133 of outer balloon member 101 may be attached directly to distal end 137 of inner balloon member 103. Once outer balloon member 101 is attached to inner balloon member 103, inner balloon member 103 may be inverted, as shown by arrows 120 to form occlusion balloon 100 as shown in FIG. 1A. In some cases, before or after being attached to inner balloon member 103, outer balloon member 101 may be a hollow tube. Accordingly, at some point in the process of forming occlusion balloon 100, one end of outer balloon member 101 may be sealed.

In other embodiments, occlusion balloon 100 may be formed in an integral manner, for instance by varying the specific material or material qualities, along with a diameter, during an extrusion process and/or stretching process, or other manufacturing process. In these embodiments, the manufacturing process(es) may result in a tube with varying materials or material properties and varying diameters. Accordingly, the end of outer balloon member 101 not connected to inner balloon member 103 may be sealed to form occlusion balloon 100.

In general the occlusion balloons, occlusion balloons 100 and 400, described with respect to FIGS. 1A-5 may be formed from various materials. For instance, the occlusion balloons may be made from any low durometer, elastomeric material. Examples of such material may include silicone, thermoplastic polyurethane (TPU), SIBS (poly styrene-isobutylene-styrene block copolymer), polyurethane, SEBS (styrene ethylene butylene styrene block copolymer), other styrenic block copolymers, or other suitable materials. In at least some embodiments, different portions of the occlusion balloons may be made from different materials, for example to give the different portions of the balloons the different properties detailed above.

Figure 6:
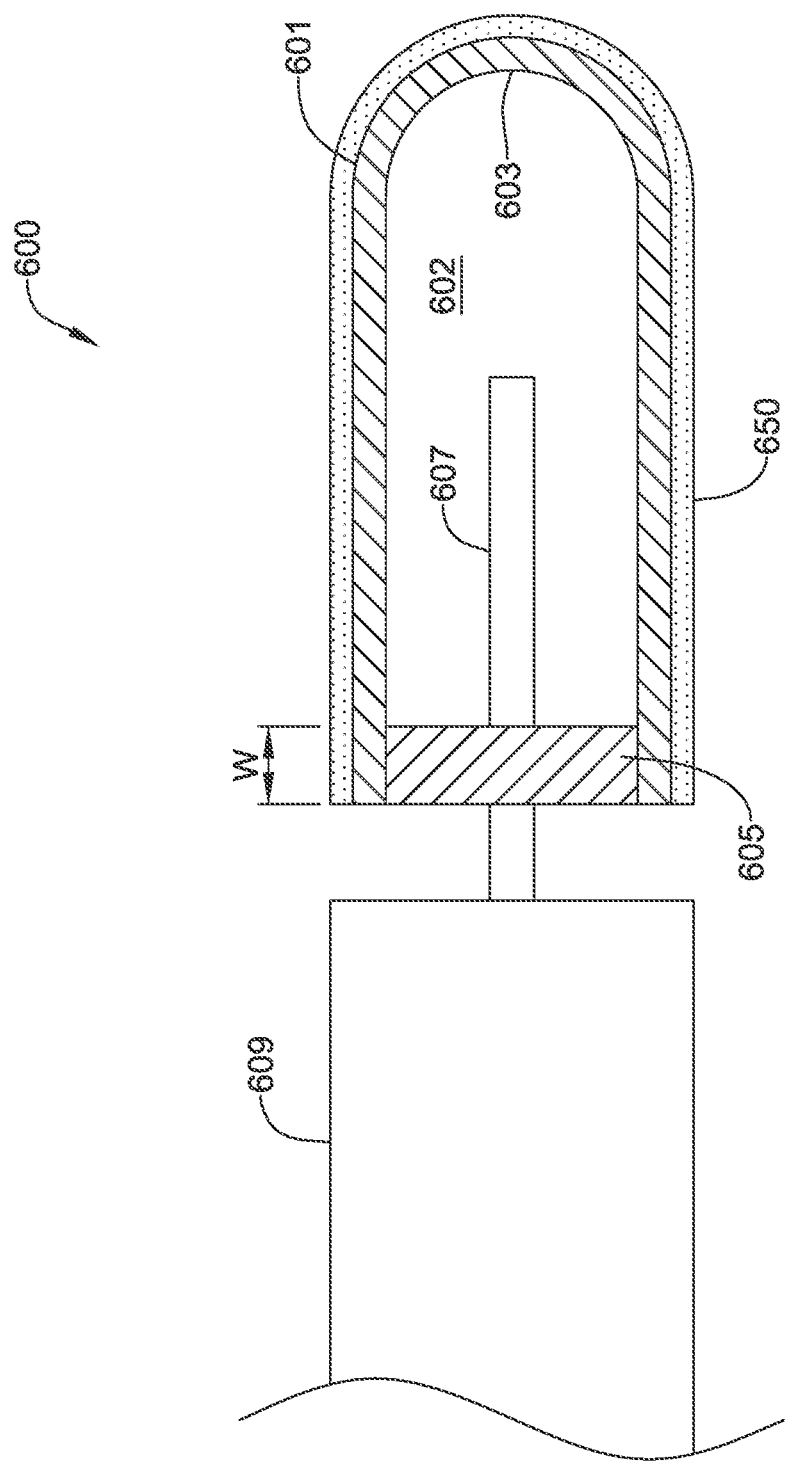
FIG. 6 depicts a cross-section of another exemplary occlusion balloon and inflation device in accordance with various embodiments of the present disclosure.

FIG. 6 depicts an exemplary occlusion balloon 600 in an uninflated state. Similar to occlusion balloons 100 and 400, occlusion balloon 600 may be a self-sealing occlusion balloon, and may be used to occlude various vessels or arteries such as a right gastric artery, a gastroduodenal artery, right or left hepatic arteries, or gonadal veins. However, in other instances, occlusion device 600 may be used to occlude other body lumens, such as other arteries or vessels, or various vascular anomalies such as gastric varices. Occlusion balloon 600 may have outer wall 601 and inner wall 603. Occlusion balloon 600 may additionally include solid self-sealing member 605 at a proximal end thereof.

In some embodiments, occlusion balloon 600 may be formed from an extruded hollow tubular member. Some applications of occlusion balloon 600 may be for the occlusion of small branch arteries or vessels. Accordingly, in some instances, the hollow tube may have a relatively small outer diameter, for example between 0.10 inches (2.54 mm) to 0.25 inches (6.35 mm). However, where occlusion balloon 600 is used in other applications, the hollow tube may have a larger diameter suited to those other applications. Additionally, the hollow tube may be formed from any low durometer, elastomeric material. Examples of such material may include silicone, thermoplastic polyurethane (TPU), SIBS (poly styrene-isobutylene-styrene block copolymer), polyurethane, SEBS (styrene ethylene butylene styrene block copolymer), other styrenic block copolymers, or other suitable materials.

During or after formation of the hollow tube, one end of the hollow tubular member may be sealed. For instance, the hollow tube may be inserted over a mandrel, and one end may be thermally processed (e.g., laser welded) to produce a taper on one end and to seal the tapered end.

Either before or after one end of the hollow tubular member is sealed, self-sealing member 605 may be inserted into the end of the tubular member that is not sealed (or will not be sealed) and bonded to the tubular member. Self-sealing member 605 may be bonded by an adhesive, such as a UV adhesive, by heat bonding, or by other bonding techniques known in the art.

In some instances, self-sealing member 605 may be made from the same material as the hollow tubular member. However, in other instances, self-sealing member 605 may be made from a different material than the hollow tubular member. Example materials include silicone, thermoplastic polyurethane (TPU), SIBS (poly styrene-isobutylene-styrene block copolymer), polyurethane, SEBS (styrene ethylene butylene styrene block copolymer), other styrenic block copolymers, or other suitable materials. In some embodiments, self-sealing member 605 may be a thin membrane that is only about 0.001 inch to about 0.02 inches (0.025 mm to about 0.5 mm) wide, as defined by width W in FIG. 6. However, in other embodiments, self-sealing member 605 may be wider and may have a width on the order of about 0.1 inches (2.54 mm) or more.

Generally, self-sealing member 605 may have self-sealing properties. For instance, if a small diameter member punctures through self-sealing member 605 and is then removed, self-sealing member 605 member may maintain a seal. In some instances, self-sealing member 605 may be able to maintain a seal after being punctured by members that have diameters ranging between about 0.010 inches to 0.015 inches (0.254 mm to 0.381 mm).

In some embodiments, occlusion balloon 600 may further include adhesive 650 disposed on outer wall 601. Adhesive 650 may be a biologically safe adhesive and may act as a tissue sealant or a mucosal adhesive. Some example biologically safe adhesives include hydrogels comprised of polymers. One example hydrogel is a copolymer of vinyl pyrrolidone, acrylic acid, and N-hydroxysuccinimide. An example structure of such a copolymer is shown below:

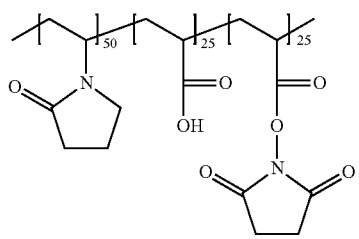

Other example biologically safe adhesives include biomimetic adhesives comprising synthetic hydrogels (PEO as one example) modified with catechol functionality (mussel-like adhesives), and cross-linked polyacrylic acid and copolymers. Once occlusion balloon 600 is positioned within the artery or vessel and inflated, the adhesive 650 may aid in securing occlusion balloon 600 within the artery or vessel. It should be understood that although only occlusion balloon 600 is described herein as including an adhesive, such as adhesive 650, any occlusion balloon or device described herein may have a similar adhesive disposed on an outer wall or outer balloon member of the occlusion balloon or device.

FIG. 6 also depicts inflation device 609. Inflation device 609 may generally be an elongated device with one or more inflation lumens extending throughout inflation device 609. In examples where occlusion balloon 600 is to be used within small diameter arteries or vessels, inflation device 609 may have a diameter of about 0.025 inches (0.635 mm). However, where occlusion balloon 600 is used in other applications, inflation device 609 may have a larger or smaller diameter suited to those other applications. For instance, in various embodiments, inflation device 609 may have a diameter ranging from about 0.01 inches (0.254 mm) to about 0.25 inches (6.35 mm). In some examples, inflation device 609 may be a catheter or microcatheter and may include one or inflation lumens extending through the length of inflation device 609. Different portions of inflation device 609 may have varying levels of rigidity. For instance, a proximal portion of inflation device 609 may have a relatively high rigidity, while a distal portion of inflation device 609 may have a relatively low level of rigidity. These differing levels of rigidity may allow for a user, such as a physician, to apply pushing forces to inflation device 609, yet allow at least the distal portion of inflation device 609 to bend through potentially tortuous paths to be positioned at a desired implant site.

Inflation device 609 may additionally have a penetration member or needle 607 extending from the distal end of inflation device 609. In some embodiments, needle 607 may have a diameter between about 0.010 inches to about 0.015 inches (0.254 mm to 0.381 mm), and in some specific embodiments, needle 607 may have a diameter of about 0.014 inches (0.356 mm). Needle 607 may have a lumen extending therethrough that may be in communication with the one or more lumens extending through inflation device 609. Needle 607 may be made from any suitable material, such as a metal like stainless steel or titanium, or from a biocompatible polymer that has sufficient rigidity to puncture self-sealing member 605. Needle 607 may have any suitable length, and in some embodiments may be about as long as occlusion balloon 600.

To deliver occlusion balloon 600, occlusion balloon 600 may be positioned on the distal end of inflation device 609 with penetration member or needle 607 puncturing self-sealing member 605. The friction between needle 607 and self-sealing member 605 may keep occlusion balloon 600 secured to inflation device 609 during delivery, or another securement mechanism may be used to secure occlusion balloon 600 to inflation device 609. Although depicted in FIG. 6 with a gap between occlusion balloon 600 and inflation device 609, in some cases occlusion balloon 600 may be disposed on inflation device 609 such that there is no gap. With occlusion balloon 600 disposed on inflation device 609, a user, such as a physician, may maneuver inflation device 609 to a desired implantation site. Once positioned at the desired implant site, inflation media may be delivered through the one or more inflation lumens of inflation device 609, including through penetration member or needle 607, and into lumen 602 of occlusion balloon 600.

Figure 7:
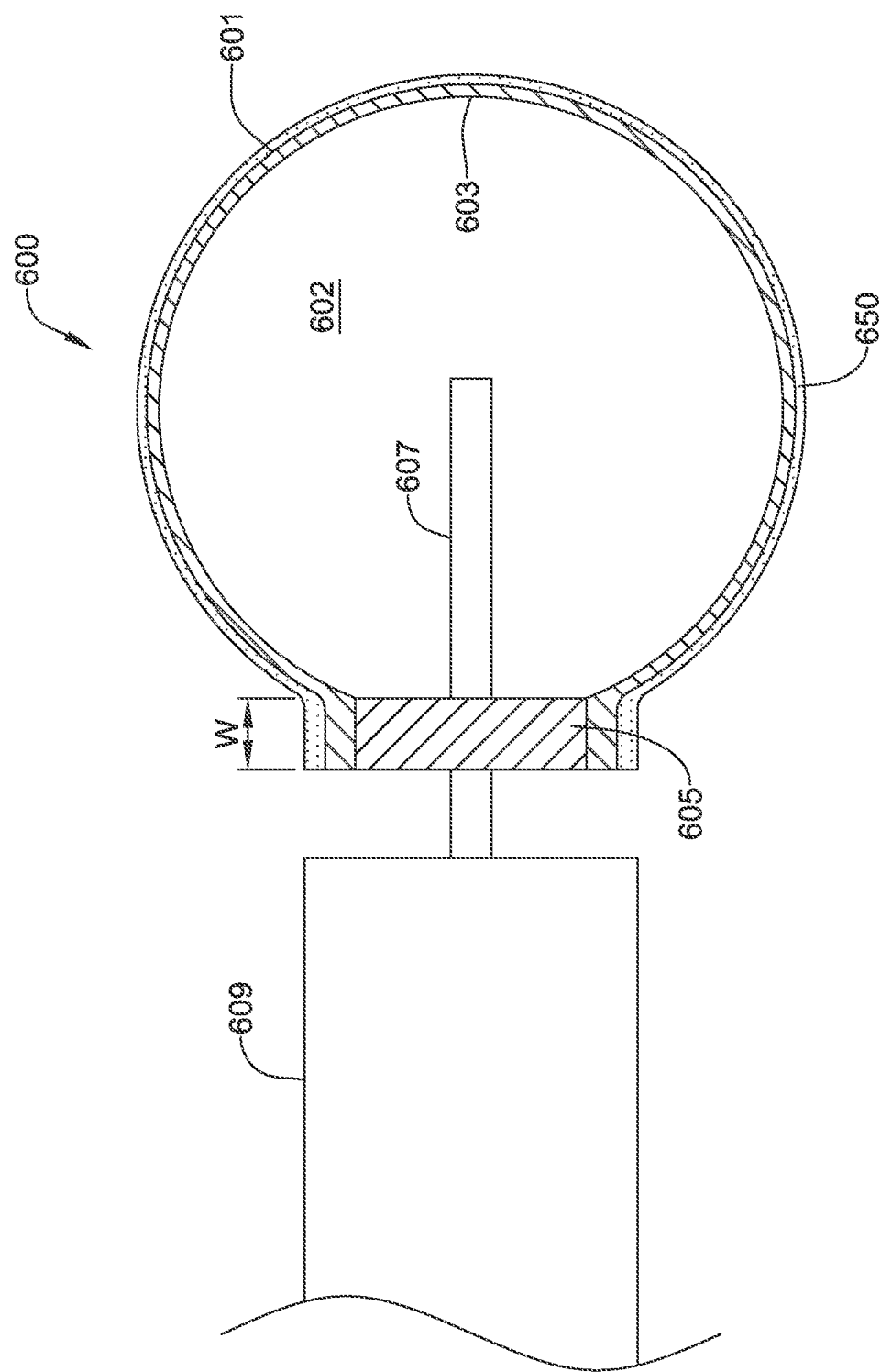
FIG. 7 depicts a cross-section of the occlusion balloon of FIG. 6 in an inflated state.

FIG. 7 depicts occlusion balloon 600 in an inflated state. Delivering inflation media into lumen 602 may increase the pressure inside occlusion balloon 600. Since occlusion balloon 600 is made from an elastomeric material, occlusion balloon 600 may be compliant. As the pressure inside occlusion balloon 600 increases, walls 601, 603 may stretch and expand, and occlusion balloon 600 may become inflated. Because of the diameter of needle 607 and the physical properties of self-sealing member 605, as the inflation media is delivered into occlusion balloon 600, self-sealing member 605 maintains a seal and prevents inflation media from escaping lumen 602.

Figure 8:
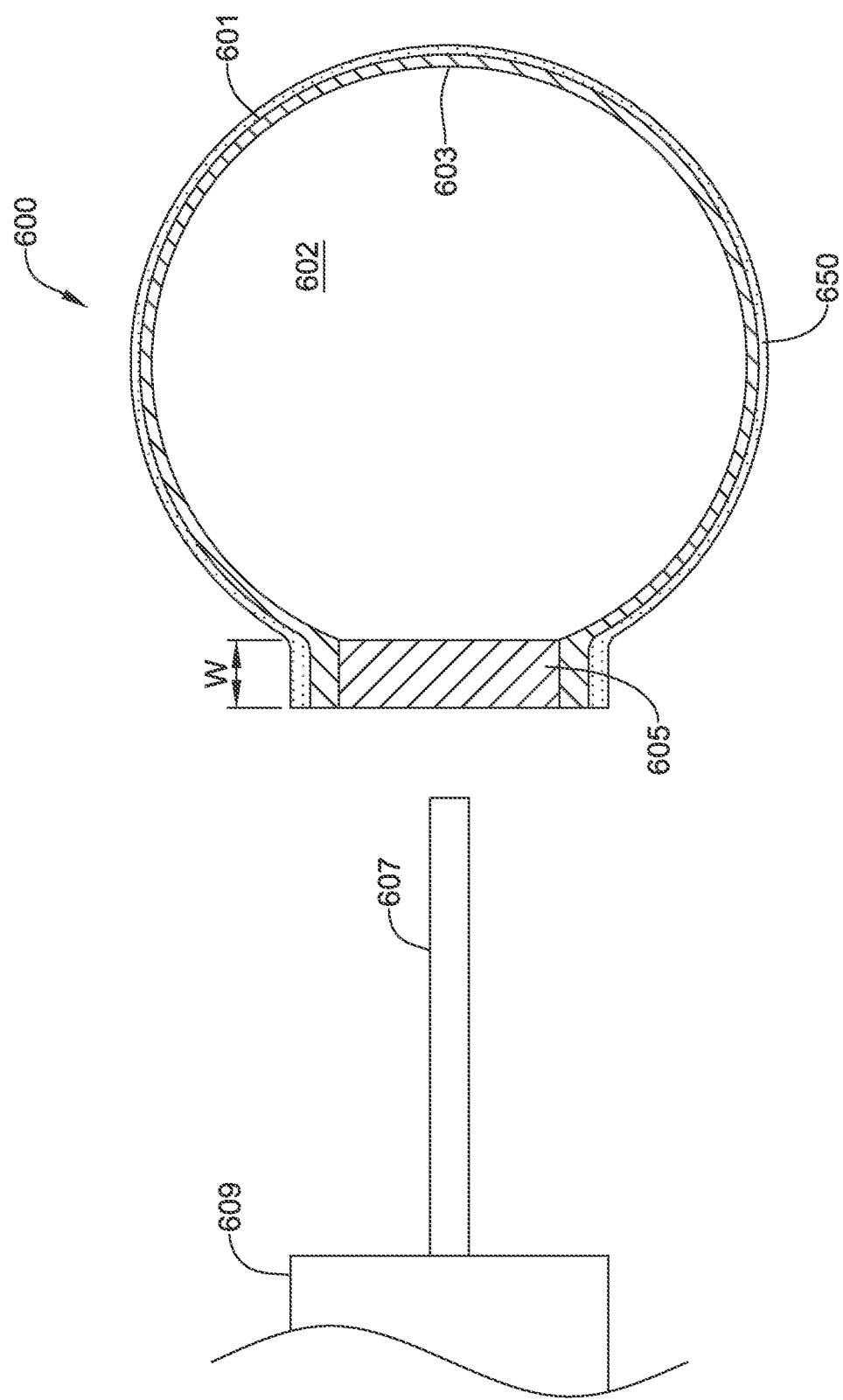
FIG. 8 depicts another cross-section of the occlusion balloon of FIG. 6 in an inflated state.

Once occlusion balloon 600 has reached a desired size, for instance a sufficient size to fully occlude the artery or other vessel (not shown) in which occlusion balloon 600 is disposed, needle 607 may be retracted from self-sealing member 605, as shown in FIG. 8. For instance, the inflated occlusion balloon 600 may press against the walls of the body lumen (e.g., artery or vessel) where occlusion balloon 600 is disposed. The friction between the walls of the body lumen (e.g., artery or vessel) and the outer wall 601 of occlusion balloon 600 be may be greater than the friction between needle 607 and self-sealing member 605. As needle 607 is retracted, the friction between the body lumen and the outer wall 601 of occlusion balloon 600 maintains occlusion balloon 600 in place. Additionally, because of the diameter of needle 607 and the physical properties of self-sealing member 605, after needle 607 is retracted from self-sealing member 605, self-sealing member 605 maintains a seal of lumen 602. Accordingly, the inflation media inside lumen 602 may not escape through self-sealing member 605.

Figure 9:
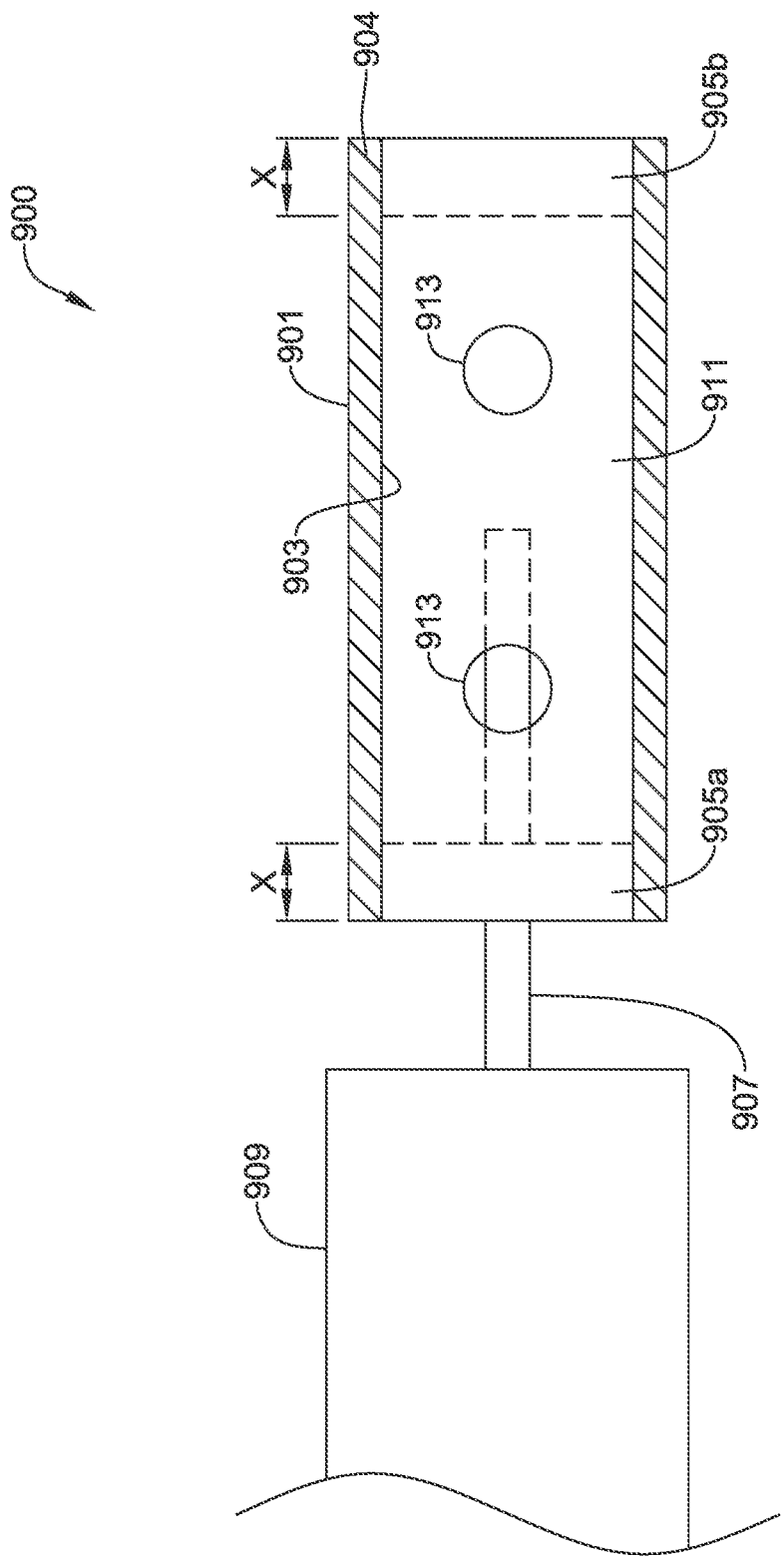
FIG. 9 is a partial cross-sectional view of an exemplary occlusion device and inflation device in accordance with various embodiments of the present disclosure.

FIG. 9 is an embodiment of an occlusion device, occlusion device 900, which may also be used for occlusion of various vessels or arteries such as a right gastric artery, a gastroduodenal artery, right or left hepatic arteries, or gonadal veins. However, in other instances, occlusion device 900 may be used to occlude other body lumens, such as other arteries or vessels, or various vascular anomalies such as gastric varices. Occlusion device 900 may include balloon member 904 having outer wall 901 and inner wall 903. Generally, balloon member 904 may be made from any low durometer, elastomeric material. Examples of such material may include silicone, thermoplastic polyurethane (TPU), SIBS (poly styrene-isobutylene-styrene block copolymer), polyurethane, SEBS (styrene ethylene butylene styrene block copolymer), other styrenic block copolymers, or other suitable materials.

Balloon member 904 is shown in cross-section in FIG. 9 and may be disposed around inner member 911, which is shown in plan-view. Inner member 911 may be a hypotube or other hollow tube structure and may be formed from a metal such as stainless steel or titanium, or from any number of suitable polymer or other materials. In some cases, occlusion device 900 may be used to occlude small arteries or vessels. In such instances, inner member 911 may have a diameter between about 0.004 inches to about 0.21 inches (0.10 mm to 0.53 mm). However, where occlusion device 900 is used in other applications, the inner member 911 may have a larger diameter suited to those other applications. Additionally, inner member 911 may include ports 913 that communicate with an inner lumen of inner member 911. Although shown as generally round, ports 913, in other embodiments, may take other shapes such as slots or the like.

Occlusion device 900 may additionally include self-sealing members 905a, 905b, indicated by dashed lines in FIG. 9. Generally, self-sealing members 905a, 905b may be disposed at each end of inner member 911. Self-sealing members 905a, 905b may be formed from materials such as silicone, thermoplastic polyurethane (TPU), SIBS (poly styrene-isobutylene-styrene block copolymer), polyurethane, SEBS (styrene ethylene butylene styrene block copolymer), other styrenic block copolymers, or other suitable materials. In some embodiments, self-sealing member 905a, 905b may be a thin membrane that is about 0.001 inch to about 0.02 inches (0.025 mm to about 0.5 mm) wide, as defined by width X in FIG. 9. However, in other embodiments, self-sealing members 905a, 905b may be wider and may have a width on the order of about 0.1 inches (2.54 mm) or more.

To form occlusion device 900, in some embodiments, balloon member 904 may be extruded directly over inner member 911, or otherwise placed over inner member 911. Ends of balloon member 904 may then be bonded to the ends of inner member 911, for example with various adhesives or by heat bonding or the like. Self-sealing members 905a, 905b may be inserted into and/or adjacent each end of inner member 911 and bonded to inner member 911. As some examples, self-sealing members 905a, 905b may be adhesively bonded or heat bonded to inner member 911.

FIG. 9 also depicts inflation device 909. Inflation device 909 may generally be an elongated device with one or more inflation lumens extending throughout inflation device 909. In examples where occlusion device 900 is to be used within small diameter arteries or vessels, inflation device 909 may have a diameter of about 0.027 inches (0.686 mm). However, where occlusion device 900 is used in other applications, inflation device 909 may have a larger diameter suited to those other applications. In some examples, inflation device 909 may be a catheter or microcatheter and may include one or inflation lumens extending through the length of inflation device 909. Different portions of inflation device 909 may have varying levels of rigidity. For instance, a proximal portion of inflation device 909 may have a relatively high rigidity, while a distal portion of inflation device 909 may have a relatively low level of rigidity. These differing levels of rigidity may allow for a user, such as a physician, to apply pushing forces to inflation device 909, yet allow at least the distal portion of inflation device 909 to bend through potentially tortuous paths to be positioned at a desired implant site.

Inflation device 909 may additionally have a penetration member or needle 907 extending from the distal end of inflation device 909. In some embodiments, needle 907 may have a diameter between about 0.010 inches to about 0.015 inches (0.254 mm to 0.381 mm), and in some specific embodiments, needle 907 may have a diameter of about 0.014 inches (0.356 mm). Needle 907 may have a lumen extending therethrough that may be in communication with the one or more lumens extending through inflation device 909. Needle 907 may be made from any suitable material, such as a metal like stainless steel or titanium, or from a biocompatible polymer that has sufficient rigidity to puncture self-sealing member 905a. Needle 907 may have any suitable length, and in some embodiments may be slightly shorter than occlusion device 900. For instance, a maximum length of needle 907 would be a length such that when needle 907 is fully inserted into occlusion device 900 as in FIG. 9, needle 907 does not puncture self-sealing member 905b.

To deliver occlusion device 900, occlusion device 900 may be positioned on the distal end of inflation device 909 with penetration member or needle 907 puncturing self-sealing member 905a. The friction between needle 907 and self-sealing member 905a may keep occlusion device 900 secured to inflation device 909 during delivery, or another securement mechanism may be used to secure occlusion balloon 600 to inflation device 609. Although depicted in FIG. 9 with a gap between occlusion device 900 and inflation device 909, in some cases occlusion device 900 may be disposed on inflation device 909 such that there is no gap. With occlusion device 900 disposed on inflation device 909, a user, such as a physician, may maneuver inflation device 909 to a desired implantation site. Once positioned at the desired implant site, inflation media may be delivered through the one or more inflation lumens of inflation device 909, including through penetration member or needle 607, and into inner member 911. The inflation media may then exit inner member 911 through ports 913 and into a lumen defined by balloon member 904. Delivering inflation media into balloon member 904 may increase the pressure inside occlusion device 900. Because balloon member 904 is made from an elastomeric material, balloon member 904 may be compliant. Accordingly, as the pressure inside balloon member 904 increases, walls 901, 903 may stretch and expand, and occlusion device 900 may inflate.

Figure 10:
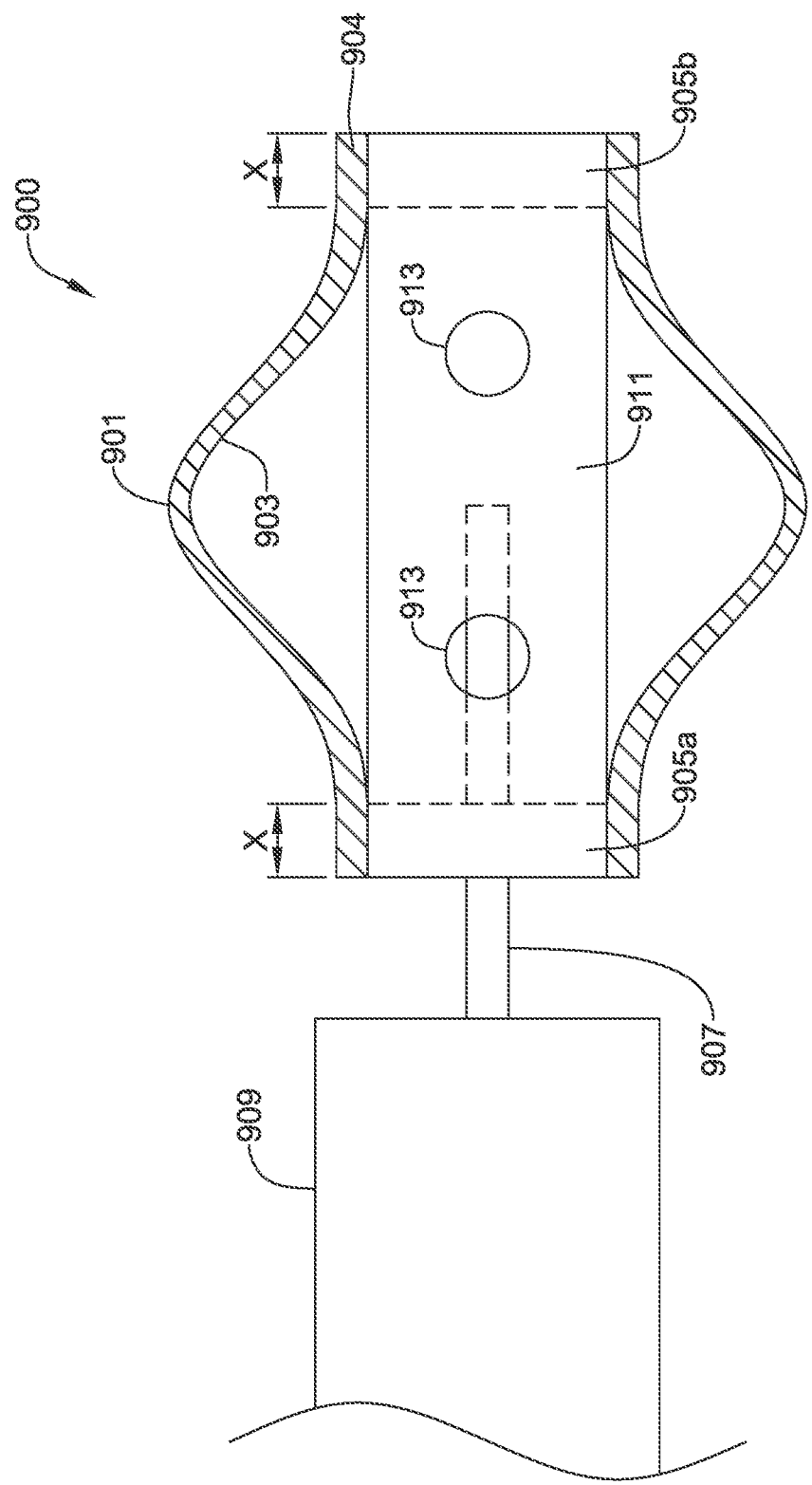
FIG. 10 is a partial cross-sectional view of the occlusion device of FIG. 9 in an inflated state.

FIG. 10 depicts balloon member 904 in an inflated state after inflation media has been delivered into balloon member 904. Because of the diameter of needle 907 and the physical properties of self-sealing member 905a, as the inflation media is delivered into balloon member 904, self-sealing member 905a maintains a seal and prevents inflation media from escaping from occlusion device 900.

Once occlusion device 900 has been inflated a desired size, for instance a sufficient size to fully occlude the body lumen (e.g., artery or other vessel) in which occlusion device 900 is disposed, needle 907 may be refracted from self-sealing member 905a. For instance, the inflated occlusion device 900 may press against the walls of the body lumen (e.g., artery or vessel) where occlusion device 900 was placed. In different embodiments, when inflated, occlusion device 900 may have a diameter that is between five percent and thirty percent larger than the diameter of the lumen (e.g. artery or vessel) where occlusion device is disposed. The friction between the walls of the body lumen (not shown) and the outer wall 901 of occlusion device 900 be may be greater than the friction between needle 907 and self-sealing member 905a. As needle 907 is refracted, the friction between the body lumen and the outer wall 901 of occlusion device 900 maintains occlusion device 900 in place. Additionally, because of the diameter of needle 907 and the physical properties of self-sealing member 905a, after needle 907 is retracted from self-sealing member 905a, self-sealing member 905a maintains a seal of occlusion device 900, preventing the inflation media from escaping.

Figure 11:
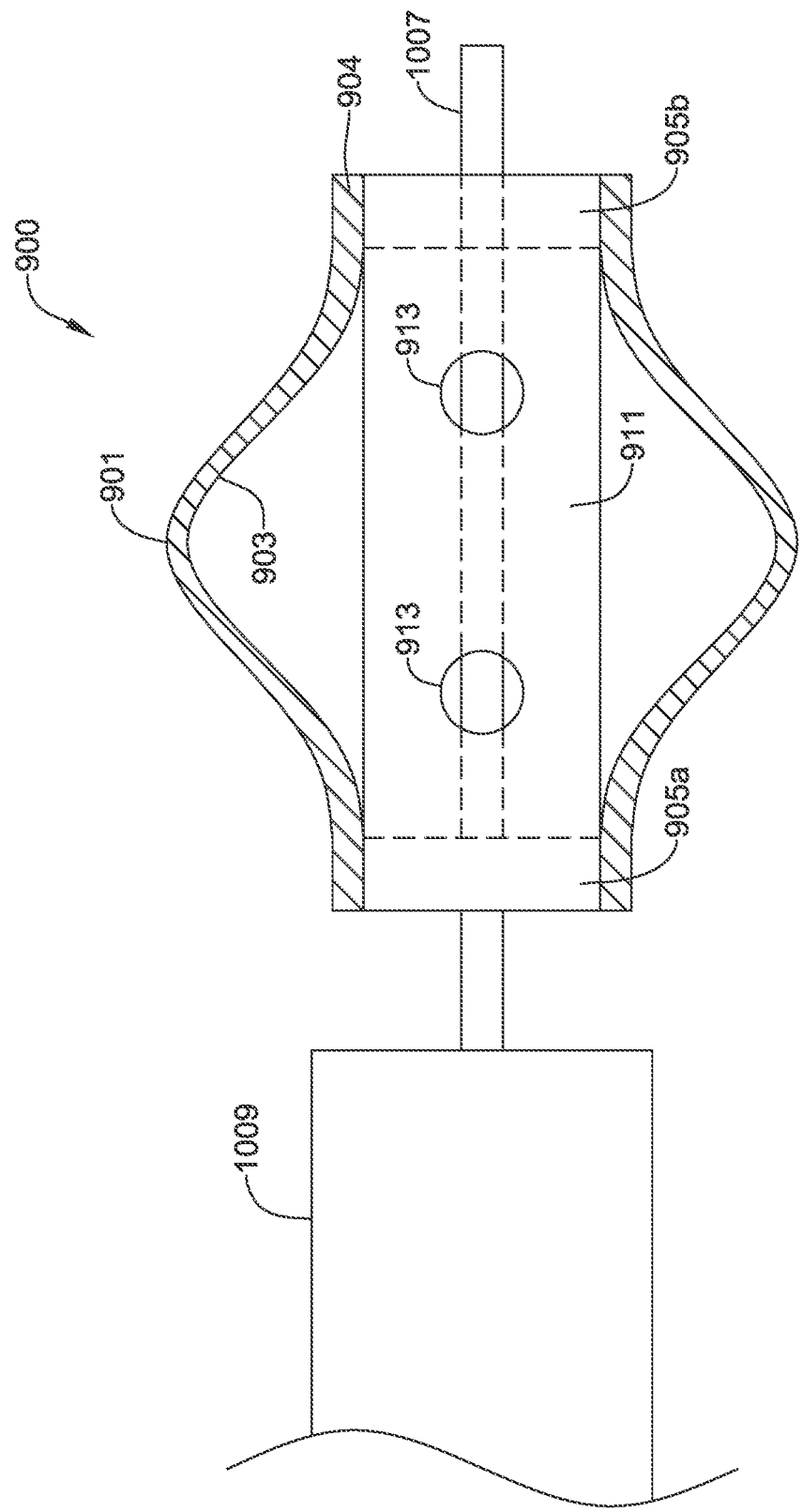
FIG. 11 is a partial cross-sectional view of the occlusion device of FIG. 9 in an inflated state with an injection device in accordance with various embodiments of the present disclosure.

After needle 907 has been retracted from self-healing member 905a, inflation device 909 may be fully retracted from the patient. In some instances, it may be beneficial to inject one or more therapeutic agents, such as liquid embolic agents, polymerizing agents, and therapeutic drugs, or particles, including loaded particles, or other flow-altering devices such as micro-coils into the patient within the artery or vessel that occlusion device 900 is occluding. Accordingly, as shown in FIG. 11, to inject one or more therapeutic agents or particles, occlusion device 900 may be used in conjunction with injection device 1009. Injection device 1009 may be generally similar to inflation device 909 in that injection device 1009 may be an elongated device with one or more inflation lumens running through injection device 1009. Additionally, injection device 1009 may have penetration member or needle 1007 extending from the distal end of injection device 1009.

Needle 1007 may generally be similar to needle 907. For instance, needle 1007 may have a similar diameter to needle 907, or at least may have a diameter in the range of about 0.010 inches to about 0.015 inches (0.254 mm to 0.381 mm). Additionally, needle 1007 may have a lumen extending therethrough which is in communication with the one or more lumens extending through injection device 1009. However, needle 1007 may generally be longer than needle 907. For instance, needle 1007 may be long enough such that when needle 1007 is inserted into occlusion device 900, needle 1007 may extend all the way through occlusion device 900, and more specifically through both proximal and distal self-sealing members 905a and 905b, as depicted in FIG. 11. In this way, a user may inject one or more therapeutic agents or particles into an artery or vessel, or other body lumen, past the point where occlusion device 900 is occluding the body lumen. Additionally, because of the diameter of needle 1007 and the physical properties of self-sealing members 905a, 905b, when needle 1007 is inserted through self-sealing members 905a, 905b, self-sealing members 905a, 905b may maintain a seal of occlusion device 900, preventing inflation media from escaping.

Generally, as described with respect to the various embodiments of occlusion balloons 100, 400, and 600, and occlusion device 900, the occlusion balloon or outermost balloon member may be elastic and stretch as the occlusion balloon or device is inflated. Accordingly, as the occlusion balloon or device is inflated, the occlusion balloon or outermost balloon member may conform to the specific artery or vessel, or other body lumen, where the occlusion balloon or device is disposed. When the occlusion balloon or device is fully inflated, an outer surface or wall of the occlusion balloon or outermost balloon member may generally be in close contact with the wall of the body lumen so as to occlude the body lumen. Accordingly, the friction between the wall of the body lumen and the occlusion balloon or outermost balloon member may act to retain the occlusion balloon or device in place within the body lumen. However, in at least some of the embodiments described above with respect to occlusion balloons 100, 400, and 600, and occlusion device 900, the occlusion balloon or outermost balloon member may have one or more retention features for aiding in retaining the occlusion balloon or device in place.

As one example, the outer surface or wall of the occlusion balloon or outermost balloon member may be textured. In these embodiments, the textured surface may act to encourage tissue in-growth into the grooves or other features of the textured surface. This tissue growth may act to further secure the occlusion balloon or device within the artery or vessel, or other body lumen.

The inflation media that may be used to inflate any of the balloons or devices described herein, such as occlusion balloons 100, 400, and 600, and occlusion device 900, may be any of a number of inflation media. For instance the inflation media could be water, saline, one or more various contrast materials, or one or more various foam-forming polymer materials, or any suitable curable material, such as multiple-part epoxies. In at least some embodiments the inflation media may comprise two or more separate reactants. Once the two or more separate reactants have mixed, the reactants may undergo a reaction and cure or harden into a solid material. In some embodiments, the curing or hardening may be aided by application of heat or electricity. In examples where the inflation media comprises foam forming polymer materials, separate reactants may be mixed together to form a solid polymer material or expanded foam. In some cases, the two or more reactants may be mixed before being delivered through the one or more inflation lumens of an inflation device that are in fluid communication with the occlusion balloon or device. In other cases, however, the two or more separate reactants may be delivered through separate inflation lumens and only mix together in the occlusion balloon or device where the inflation lumens open into. In still other cases, the reactants may be delivered through separate inflation lumens, and the inflation lumens may merge prior to opening into the occlusion balloon or device. In some of these cases, the inflation device may include one or more mixing features where the inflation lumens merge to aid in the mixing of the reactants. The solid polymer material or expanded foam formed by the mixing of the two or more reactants may help to prevent blood from flowing into and past the occlusion balloon or device by forming a solid embolic device.

Figure 12:
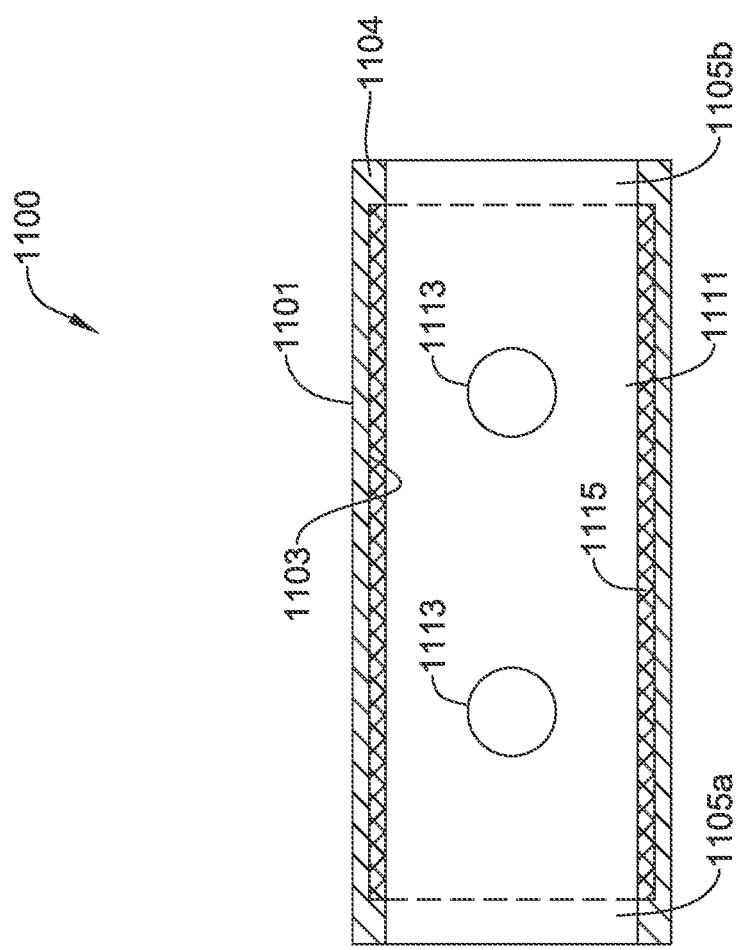
FIG. 12 is a partial cross-sectional view of another exemplary occlusion device in accordance with various embodiments of the present disclosure.
Figure 13:
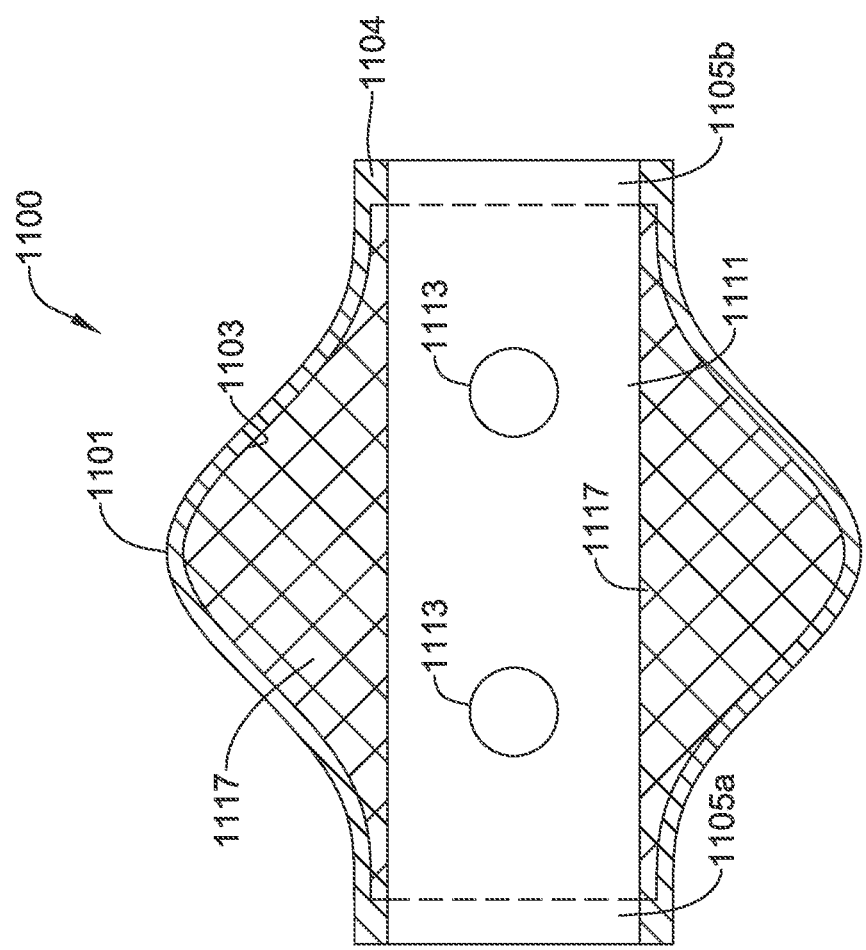
FIG. 13 is a partial cross-sectional view of the occlusion device of FIG. 12 in an inflated state.

In embodiments where the inflation media comprises polymer material reactants which, when mixed, form a foam structure, the separate polymer material reactants may begin as liquids. Once the liquid reactants are mixed together, the liquid reactants may begin to expand in a foaming fashion and eventually harden or cure. As one example, the interior of the occlusion balloon or device may be coated with a super absorbent polymer (SAP) such as lightly cross-linked poly sodium acrylate, or one or more hygroscopic polymers such as a polyether block amide like PEBAX® MV 1074 or Tecophilic® Lubrizol HP-60d, or other similar polymers, for instance as shown in FIG. 12. FIG. 12 depicts occlusion device 1100 including inner member 1111 having ports 1113 with balloon member 1104 having outer wall 1101 and inner wall 1103 disposed around inner member 1111. Occlusion device 1100 may additionally have self-sealing member 1105a, 1005b disposed at each end of inner member 1111. Occlusion device 1100 may further include polymer layer 1115 disposed directly on inner member 1111. For instance, before extruding or otherwise attaching balloon member 1104 to inner member 1111, polymer layer 1115 may be sprayed onto inner member 1111, or inner member 1111 may be dipped into a polymer material to coat inner member in polymer layer 1115. Balloon member 1104 may then be extruded and/or attached to inner member 1111 over polymer layer 1115. In this manner, when inflation media is delivered into inner member 1111 and through ports 1113 into the interior of balloon member 1104, the inflation media will contact polymer layer 1115. In some examples, polymer layer 1115 may be a SAP. Accordingly, when the occlusion balloon or device is inflated with water, polymer layer 1115 swells resulting in gelation of the inflation media, resulting in solid material 1117, as seen in FIG. 13.

In other embodiments, the inflation media may comprise an aqueous solution (e.g. 1% solids) of polyacrylic acid which is injected into the occlusion balloon or device through a first inflation lumen of an inflation device and an aqueous solution of base (e.g. NaOH or sodium bicarbonate) which is injected through a second inflation lumen of an inflation device. Mixing of the two solutions may result in neutralization of the polyacrylic acid and form gelled polysodium acrylate.

In still other embodiments, a foam may be formed using a reaction according to equation (1).

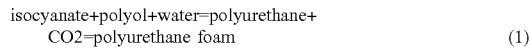

$$\text{isocyanate} + \text{polyol} + \text{water} = \text{polyurethane} + CO_2 = \text{polyurethane foam} \tag{1}$$

Example isocyanates that may be used include hexamethyline diisocyanate (HDI), toluene diisocyanate (TDI), xylene diisocyanate, methylene diphenyl diisocyanate (MDI), lysine diisocyanate, and isophorone diisocyanate. Example polyols that may be used include polyether, polybutadiene polyols, polysiloxane polyols, polypropylene glycols (PPG), and polyethylene glycols (PEG).

In general, by utilizing different reactants or reactants in varying proportions, foams or gelated materials having specific, differing properties may be formed. For instance, various foams used to inflate the occlusion balloon or device may have pore sizes ranging from 5-500 micrometers and may have anywhere between 10-10,000 cells. Further, the stiffness of the foam or gelated material may be controllable based on the types and quantities of the reactants used.

Instead of delivering inflation media into the occlusion balloon or device, or in conjunction with delivering inflation media into the occlusion balloon or device, in some embodiments the occlusion balloon or outermost balloon member may be porous to blood. For example, the occlusion balloon or outermost balloon member may have one or more micro-pin holes extending therethrough. In these embodiments, a patient's blood may be able to seep into the occlusion balloon or device. In these embodiments, after entering the occlusion balloon or device, the blood may coagulate and form a thrombus, thereby forming the occlusion balloon or device into a semi-solid embolic device. In some of these embodiments, one or more thrombus-forming compounds may be disposed within the occlusion balloon or device or delivered into the occlusion balloon or device through an inflation lumen. The thrombus-forming compound may interact with the blood to speed up the coagulation and thrombus-forming process.

In still some additional or alternative embodiments, the inflation media may include one or more radiopaque materials. These radiopaque materials may show up in a relatively clear fashion on various medical imaging systems, thereby allowing for easier viewing of the occlusion balloon or device within the patient on such medical imaging systems. In some additional or alternative embodiments, various radiopaque materials may be incorporated into one or more of the walls of the occlusion balloon or device. These radiopaque materials may allow a user to view the occlusion balloon or device on a medical imaging system before injection of any inflation media.

Figure 14:
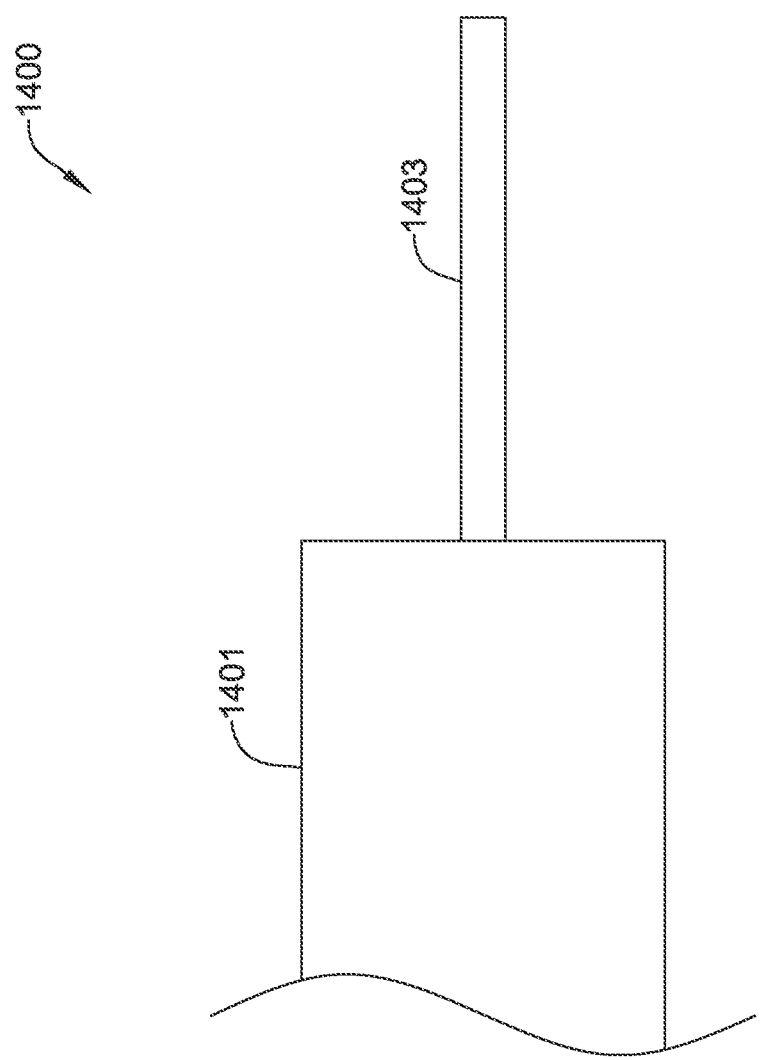
FIG. 14 is a side plan view of an exemplary retrieval device in accordance with various embodiments of the present disclosure.

In some embodiments, the occlusion balloon or device may be retrievable after implantation. To retrieve the occlusion balloon or device, a user, such as a physician, may use a device such as retrieval device 1400, a distal end of which is shown in FIG. 14. FIG. 14 depicts retrieval device 1400 as having body 1401 and tip 1403 extending from the distal end of body 1401. In general, retrieval device 1400 may be similar to inflation devices 609 and 909 in that retrieval device 1400 may be an elongate device having one or more lumens extending through the length of retrieval device 1400. Additionally, different portions of body 1401 may have varying levels of rigidity. For instance, a proximal portion of body 1401 may have a relatively high rigidity, while the distal portion of body 1401 may have a relatively low level of rigidity. These differing levels of rigidity may allow for a user, such as a physician, to apply pushing forces to body 1401, yet allow at least the distal portion of body 1401 to bend through potentially tortuous paths to be able to traverse to the implant site. Tip 1403 may generally have a smaller diameter than body 1401 and may also have a lumen extending therethrough that is in communication with the one or more lumens extending through body 1401. In some embodiments, penetration member or tip 1403 may be similar to needles 607 and 907. In at least some embodiments, retrieval device 1400 may be the same as inflation devices 609 and 909.

To retrieve an implant, retrieval device 1400 may be advanced through the vasculature of the patient to the implant site, where tip 1403 may be inserted into the occlusion balloon or device, for instance any of occlusion balloons 100, 400, or 600, or occlusion devices 900 and 1100. Once inserted into the occlusion balloon or device, a vacuum may be applied to the one or more lumens which may extract the inflation media inside the occlusion balloon or device. In embodiments where a solid or gel material was formed within the occlusion balloon or device, before applying the vacuum one or more reagents may be delivered into the occlusion balloon or device. For instance, where the occlusion balloon or device included the SAP sodium polyacrylate, which formed a gel after the occlusion balloon or device was inflated with water, a saline solution may be delivered into the occlusion balloon or device. The saline solution will return the gelled sodium polyacrylate to a liquid, which may then be withdrawn from the occlusion balloon or device by a vacuum. Once any inflation media or other material has been removed from inside the occlusion balloon or device, the vacuum may still be maintained. The maintained vacuum may provide enough suction force to hold the occlusion balloon or device onto tip 1403, for example. Retrieval device 1400 may then be withdrawn from the patient, with the occlusion balloon or device disposed on tip 1403.

Figure 15:
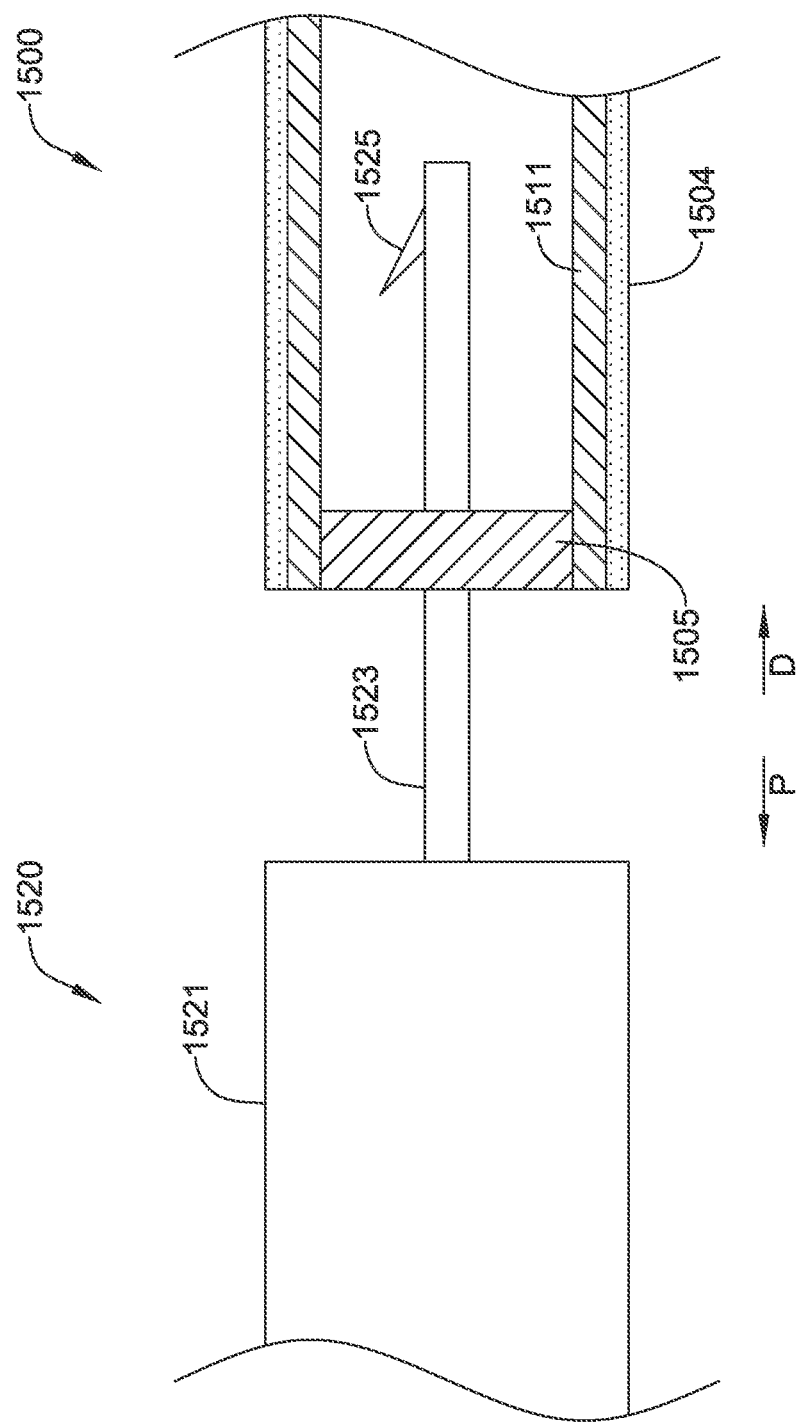
FIG. 15 is a cross-section of another exemplary retrieval device in accordance with various embodiments of the present disclosure.

In other embodiments, a retrieval device may have one or more retrieval members, for instance such as those shown in FIG. 15 with respect to retrieval device 1520. FIG. 15 depicts retrieval device 1520 attached to occlusion device 1500. Occlusion device 1500, shown in cross-section, includes balloon member 1504 disposed around inner member 1511 and self-sealing member 1505. Retrieval device 1520 comprises body 1521 and penetration member or tip 1523. Generally, retrieval device 1520 may be similar to retrieval device 1400 and/or inflation device 609 and 909. However, retrieval device 1520 may additionally include retention member 1525. In some examples, retention member 1525 may be an angled projection that is angled in a proximal direction away from the distal end of tip 1523 and toward body 1521, with the proximal direction indicated by arrow P and the distal direction indicated by arrow D in FIG. 15. For instance, retention member 1525 may be a projection (e.g., barb, prong, spur, thorn) or the like. Generally, retention member 1525 may be configured such that tip 1523, including retention member 1525, may be able to be inserted through self-sealing member 1525 as tip 1523 travels in a distal direction in relation to occlusion device 1500, as shown in FIG. 15. However, retention member 1525 may be configured such that, as retrieval device 1520 is withdrawn in a proximal direction to remove occlusion device 1500, retention member 1525 is unable to easily pass through self-sealing member 1505 in the proximal direction. For instance, the force required to pull tip 1523, including retention member 1525, through self-sealing member 1505 may be greater than the force holding occlusion device 1500 in place within an artery or vessel. Accordingly, as retrieval device 1520 is withdrawn in the proximal direction, retention member 1525 may catch on self-sealing member 1505 and pull occlusion device 1500 along with retrieval device 1520. Although shown as a having a single retention member, in other embodiments, tip 1523 may have multiple retention members disposed along various portions of tip 1523. Additionally, it should be understood that the exact shape or configuration of retention member 1525 may vary in embodiments other than that shown in FIG. 15.

Figure 16:
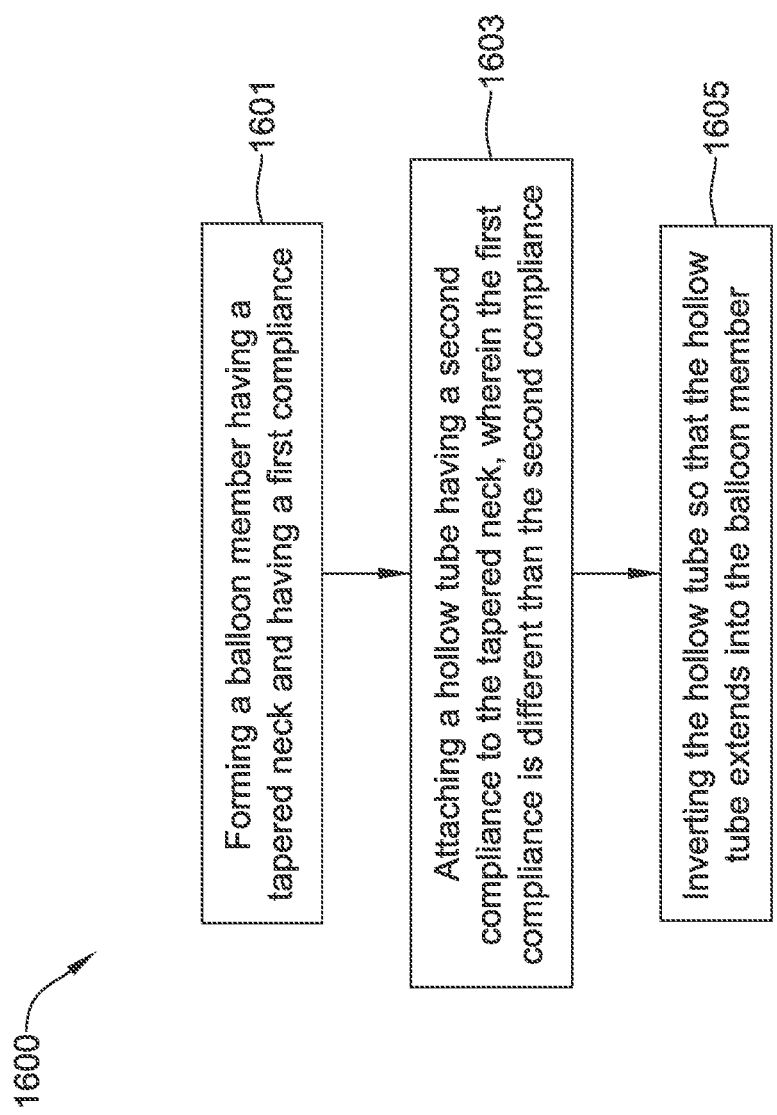
FIG. 16 is a flow diagram of an exemplary method for forming an occlusion device, such as any of the occlusion balloons or devices of FIGS. 1A-12.

FIG. 16 is a flow diagram of an exemplary method 1600 for forming an occlusion device, for instance any of the occlusion balloons or devices described herein. Method 1600 may begin with forming a balloon member having a tapered neck and having a first compliance, as at 1601. Method 1600 may then continue with attaching a hollow tube having a second compliance to the tapered neck, wherein the second compliance is different than the first compliance, as at 1603. In some embodiments, the second compliance may be greater than the first compliance, although in other embodiments, the second compliance may be less than the first compliance. Finally, method 1600 may conclude by inverting the hollow tube so that the hollow tube extends into the balloon member, as at 1605. In some instances, method 1600 may further include attaching a hollow tubular member having a third compliance to the tapered neck, and attaching the hollow tube having the second compliance to the hollow tube having the third compliance. In these embodiments, the third compliance may be less than both the first and second compliance. However, in other embodiments, the third compliance may only be less than the second compliance.

Figure 17:
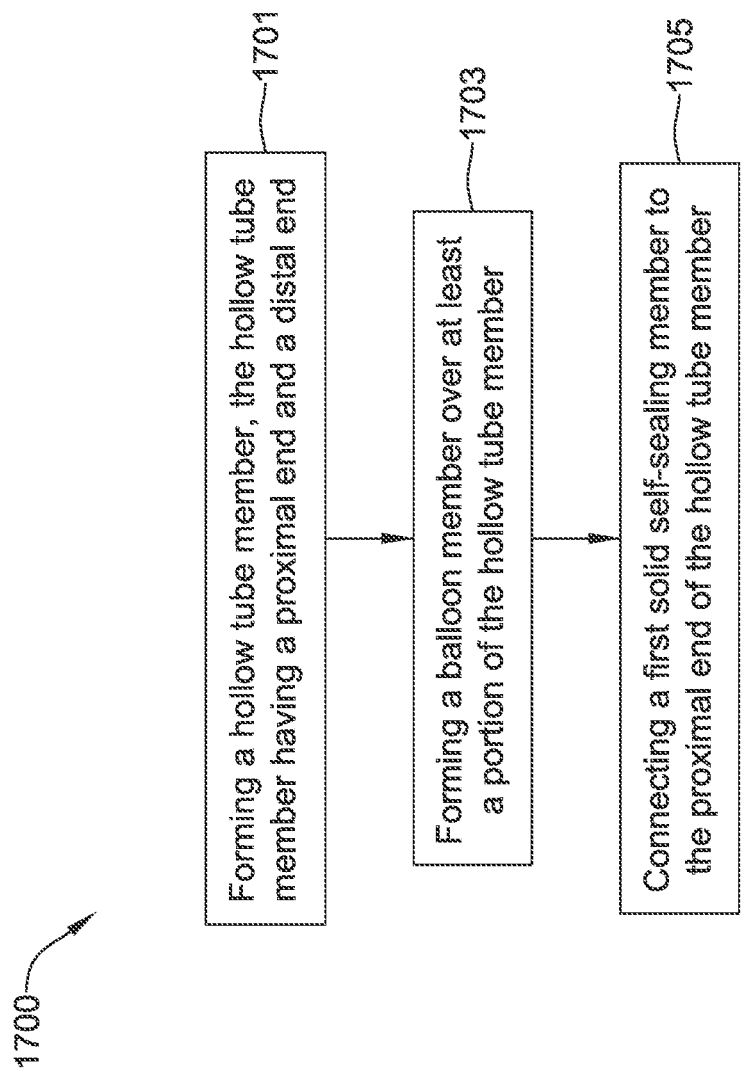
FIG. 17 is a flow diagram of another exemplary method for forming an occlusion device, such as any of the occlusion balloons or devices of FIGS. 1A-12.

FIG. 17 is another flow diagram of an exemplary method, method 1700, for forming an occlusion device, such as any of the occlusion balloons or devices described herein. Method 1700 may begin with forming a hollow tubular member, the hollow tubular member having a proximal end and a distal end, as at 1701. Method 1700 may continue with forming a balloon member over at least a portion of the hollow tubular member, as at 1703. In some embodiments, the balloon member may be secured to the hollow tubular member with an adhesive or another method of bonding. Additionally, the balloon member may generally be compliant and configured to expand under a sufficient level of internal pressure. Finally, method 1700 may include connecting a first solid self-sealing member to the proximal end of the hollow tubular member, as at 1705. In some embodiments, the solid self-sealing member may be able to maintain a seal after being punctured by members that have diameters ranging between about 0.010 inches to about 0.015 inches (0.254 mm to 0.381 mm), for example. In some additional embodiments, method 1700 may include forming one or more inflation ports on the hollow tubular member. Additionally, in some embodiments, method 1700 may further include sealing the distal end of the hollow tubular member or connecting a second solid self-sealing member to the distal end of the hollow tubular member.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope and spirit of the present disclosure as described in the appended claims.

What is claimed is:

1. An occlusion balloon comprising:
an outer balloon member; and
an inner balloon member having an inner wall and an outer wall and extending through at least a portion of the outer balloon member;
wherein, when the occlusion balloon is in a steady-state configuration forces acting on the inner wall of the inner balloon member equal forces acting on the outer wall of the inner balloon member, the inner balloon member defines a lumen having a distal end that is open to an interior of the outer balloon member.

2. The occlusion balloon of claim 1, wherein the inner balloon member forms a seal when the occlusion balloon is inflated.

3. The occlusion balloon of claim 1, wherein when forces acting inward on the outer wall of the inner balloon member are greater than forces acting outward on the inner wall of the inner balloon member, the inner wall of the inner balloon member collapses together.

4. The occlusion balloon of claim 3, wherein when the inner wall of the inner balloon member collapses together, the inner balloon member forms a seal.

5. The occlusion balloon of claim 1, wherein when forces acting inward on the outer wall of the inner balloon member are greater than forces acting outward on the inner wall of the inner balloon member, the inner wall of the inner balloon member collapses against the outer balloon member.

6. The occlusion balloon of claim 1, wherein the inner balloon member is attached to the outer balloon member.

7. The occlusion balloon of claim 1, wherein the outer balloon member folds inward at one end to form the inner balloon member.

8. The occlusion balloon of claim 1, wherein the occlusion balloon has a proximal end and a distal end, and wherein the proximal end of the occlusion balloon comprises a funnel.

9. The occlusion balloon of claim 1, wherein the outer balloon member has a first compliance and the inner balloon member has a second compliance, wherein the first compliance is different than the second compliance.

10. The occlusion balloon of claim 9, wherein the first compliance is greater than the second compliance.

11. The occlusion balloon of claim 9, wherein the second compliance is greater than the first compliance.

12. An occlusion balloon comprising:
an outer balloon member having a proximal end and a distal end;
an inner balloon member disposed within the outer balloon member, the inner balloon member having a first opening to an exterior of the outer balloon member and a second opening to an interior of the outer balloon member; and
a first self-sealing member disposed at a proximal end of the inner balloon member.

13. The occlusion balloon of claim 12, wherein the distal end of the outer balloon member is closed.

14. The occlusion balloon of claim 12, further comprising a second self-sealing member disposed at a distal end of the inner balloon member.

15. The occlusion balloon of claim 12, wherein the first self-sealing member is configured to maintain a seal on the inner balloon member while allowing a shaft of up to 0.015 inches in diameter to pass through the first self-sealing member and into the inner balloon member.

16. The occlusion balloon of claim 12, wherein the outer balloon member is porous to blood.

17. The occlusion balloon of claim 12, wherein the first self-sealing member is comprised of one or more of:
   polyurethane; silicone; and
   styrene ethylene butylene styrene (SEBS).

* * * * *